US009029081B2

(12) United States Patent
Parsons et al.

(10) Patent No.: US 9,029,081 B2
(45) Date of Patent: *May 12, 2015

(54) CHARACTERIZATION OF N-GLYCANS USING EXOGLYCOSIDASES

(71) Applicant: Momenta Pharmaceuticals, Inc., Cambridge, MA (US)

(72) Inventors: Ian Christopher Parsons, Belmont, MA (US); Dorota A. Bulik, Winchester, MA (US); Carlos J. Bosques, Arlington, MA (US); Lakshmanan Thiruneelakantapillai, Boston, MA (US); Brian Edward Collins, Arlington, MA (US)

(73) Assignee: Momenta Pharmaceuticals, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/720,192

(22) Filed: Dec. 19, 2012

(65) Prior Publication Data

US 2013/0184180 A1  Jul. 18, 2013

Related U.S. Application Data

(63) Continuation of application No. 12/595,925, filed as application No. PCT/US2008/060343 on Apr. 15, 2008, now Pat. No. 8,361,705.

(60) Provisional application No. 60/923,688, filed on Apr. 16, 2007.

(51) Int. Cl.
| | |
|---|---|
| *C12Q 1/34* | (2006.01) |
| *F28D 15/02* | (2006.01) |
| *G06F 1/20* | (2006.01) |
| *H01L 23/427* | (2006.01) |
| *H05K 7/20* | (2006.01) |

(52) U.S. Cl.
CPC .............. *C12Q 1/34* (2013.01); *F28D 15/0266* (2013.01); *G06F 1/20* (2013.01); *G06F 2200/201* (2013.01); *H01L 23/427* (2013.01); *H05K 7/20809* (2013.01); *H01L 2924/0002* (2013.01)

(58) Field of Classification Search
CPC ................................................ C12Q 2521/531
USPC ................................................ 435/4, 14, 183
See application file for complete search history.

(56) References Cited

U.S. PATENT DOCUMENTS

2006/0057638 A1  3/2006  Bosques et al.
2006/0127950 A1  6/2006  Bosques et al.

FOREIGN PATENT DOCUMENTS

| WO | WO-03/038100 A1 | 5/2003 |
| WO | WO-2005/111627 A2 | 11/2005 |
| WO | WO-2006/114663 A1 | 11/2006 |
| WO | WO-2008/130926 A2 | 10/2008 |

OTHER PUBLICATIONS

Anumula, K., Advances in Fluorescence Derivatization Methods for High-Performance Liquid Chromatographic Analysis of Glycoprotein Carbohydrates, Analytical Biochemistry, 350(1):1-23 (2006).
Dictionary Definitions of "Sequential" and "Simultaneous", 1 (2012).
Edge, C.J. et al., Fast Sequencing of Oligosaccharides: The Reagent-Array Analysis Method, Proceedings of the National Academy of Sciences of the United States of America, 89:6336-6342 (1992).
Guile, G.R. et al., A Rapid High-Resolution High-Performance Liquid Chromatographic Method for Separating Glycan Mixtures and Analyzing Oligosaccharide Profiles, Analytical Biochemistry, 240:210-226 (1996).
Hara, S. et al., Determination of Mono-*O*-Acetylated *N*-Acetylneuraminic Acids in Human and Rat Sera by Fluorimetric High-Performance Liquid Chromatophraphy, Analytical Biochemistry, 179:162-166 (1989).
International Search Report of PCT/US2008/060343, 6 pages (Oct. 11, 2008).
Jongen, S.P. et al., N-Glycans of Recombinant Human Acid α-Glucosidase Expressed in the Milk of Transgenic Rabbits, Glycobiology, 17(6):600-619 (2007).
Küster, B. et al., Rapid Approach for Sequencing Neutral Oligosaccharides by Exoglycosidase Digestion and Matrix-Assisted Laser Desorption/Ionization Time-of-Flight Mass Spectrometry, Journal of Mas Spectrometry, 31:1131-1140 (1996).
Maley, F. et al., Characterization of Glycoproteins and Their Associated Oligosaccharides throught the Use of Endoglycosidases, Analytical Biochemistry, 180:195-204 (1989).
Mizuochi, T. et al., The Asparagine-Linkeed Sugar Chains of Subcomponent C1q of the First Component of Human Complement, The Journal of Biological Chemistry, 253(20):7404-7409 (1978).
Pace, D.L. et al., Characterization of Minor N-Linked Glycans on Antibodies Using Endo H Release and MALDI-Mass Spectrometry, Analytical Letters, 42:1711-1724 (2009).
Prime, S. and Merry, T., Exoglycosidas Sequencing of N-Linked Glycans by the Reagent Array Analysis Method (RAAM), Methods in Molecular Biology, 76:53-69 (1998).

(Continued)

*Primary Examiner* — Bin Shen
(74) *Attorney, Agent, or Firm* — Choate Hall & Stewart LLP; Brenda Herschbach Jarrell; Rolando Medina

(57) ABSTRACT

The present disclosure provides methods for analyzing structure and/or composition of N-glycans. Such methods often involve digestion of N-glycans with multiple exoglycosidases. In some embodiments, N-glycans are digested with multiple exoglycosidases simultaneously. In some embodiments, N-glycans are digested with multiple exoglycosidases sequentially. In some embodiments, methods in accordance with the present disclosure involve comparison of cleavage products of N-glycans that have been digested with multiple exoglycosidases simultaneously to N-glycans that have been digested with multiple exoglycosidases sequentially.

28 Claims, 9 Drawing Sheets

(56) References Cited

OTHER PUBLICATIONS

Royle, L. et al., Detailed Structural Analysis of NGlycans Released from Glycoproteins in SDS-PAGE Gel Bands Using HPLC Combined with Exoglycosidase Array Digestions, Methods in Molecular Biology, 125-143 (2006).

Rudd, P.M. et al., Oligosaccharide Sequencing Technology, Nature, 368:205-207 (1997).

Sutton, C.W. et al, Site-Specific Characterization of Glycoprotein Carbohydrates by Exoglycosidase Digestion and Laser Desorption Mass Spectrometry, Analytical Biochemistry, 218:34-46 (1994).

Written Opinion for PCT/US2008/060343, 9 pages (Oct. 11, 2008).

CHARACTERIZATION OF N-GLYCANS USING EXOGLYCOSIDASES

CROSS-REFERENCE TO RELATED APPLICATIONS

The present application is a continuation of U.S. application Ser. No. 12/595,925, filed Jan. 6, 2010, now U.S. Pat No. 8,361,705, which was the National Stage of International Application No. PCT/US08/60343, filed Apr. 15, 2008, which claims the benefit of U.S. Provisional Application No. 60/923,688, filed Apr. 16, 2007; the entire contents of each of which are incorporated herein by reference.

BACKGROUND

The glycosylation pattern of a glycoprotein often plays a significant role in the function of that glycoprotein. To give but a few examples, a glycoprotein's glycosylation pattern may affect its ability to fold correctly, its stability (e.g., resistance to proteolytic and/or other degradation), catalytic activity, pharmacodynamic and/or pharmacokinetic properties, and/or the ability of that glycoprotein to properly interact with other molecules. Alternatively or additionally, a glycoprotein's glycosylation pattern can affect transport and targeting of the glycoprotein. For example, a glycoproteins' glycosylation pattern may affect whether the glycoprotein remains intracellular (including, e.g., the correct targeting of the glycoprotein to the proper subcellular compartment or compartments), whether the glycoprotein will be membrane-bound and/or whether the glycoprotein will be secreted from the cell.

Current methods are often not able to detect glycan species that are present at low levels within a population of glycans. Major glycan species can prevent detection and identification of glycan species that are present at low levels. Furthermore, current methods usually cannot accurately quantify relative levels of individual glycan species within a population of glycans. Current methods may not be able to detect non-standard linkages within a population of glycans. Accordingly, methods to detect glycan species that are present at low levels within a population of glycans are needed. Methods to quantify relative levels of individual glycan species within a population of glycans are needed.

SUMMARY

The present disclosure provides methods of analyzing the composition and/or structure of N-linked glycans. Methods described herein can be used to analyze a preparation of N-glycans (e.g., a mixture of N-glycans), and to measure the relative levels within the preparation of specific structural groups and/or unusual modifications (e.g., core or antennary fucose, lactosamine extensions, high mannose and hybrid glycans, sulfation, and phosphorylation). Methods described herein may generally involve steps of obtaining an N-glycan preparation; digesting N-linked glycans with exoglycosidase enzymes to specifically cleave monosaccharides from the non-reducing ends; and analyzing the cleavage products. Comparing the results of multiple treatments with exoglycosidase enzymes (e.g., simultaneous and various sequential treatments) can provide surprising information about glycan structure, e.g., can identify glycan species that are present at very low levels in a preparation of N-glycans.

A glycan preparation may be obtained by any method available in the art. In general, obtaining an N-glycan preparation comprises steps of (1) obtaining a glycoprotein or other glycoconjugate preparation; and (2) obtaining an N-glycan preparation from the glycoconjugate preparation. A glycoconjugate (e.g., glycoprotein) preparation may be obtained from any source including, but not limited to, therapeutic formulations, commercial biological products, and biological samples.

In some embodiments, an N-glycan preparation is obtained by providing a glycoprotein population and removing N-glycans from the glycoproteins of the glycoprotein population. In some embodiments, N-glycans can be associated with a detectable label (e.g., fluorescent and/or radioactive moiety).

In some embodiments, N-glycan populations are digested with one or more exoglycosidases, and the structure and/or composition of the digestion products is analyzed. In some embodiments, exoglycosidases used in accordance with the present disclosure recognize and cleave only one particular type of glycosidic linkage. In some embodiments, exoglycosidases used in accordance with the present disclosure recognize and cleave more than one particular type of glycosidic linkage. Exemplary exoglycosidases that can be used in accordance with the present disclosure include, but are not limited to, sialidase, galactosidase, hexosaminidase, fucosidase, and mannosidase.

According to the present disclosure, an N-glycan population can be digested with any exoglycosidase. In certain embodiments, N-glycans are digested by subjecting a population of N-glycans to a plurality of exoglycosidases. For example, a population of N-glycans may be subjected to 2, 3, 4, 5, 6, 7, 8, 9, 10, or more exoglycosidases. In some embodiments, multiple exoglycosidases are administered simultaneously. In some embodiments, multiple exoglycosidases are administered sequentially. In some embodiments, varying the identity of the exoglycosidases which are administered reveals information about N-glycan structure and/or composition. In some embodiments, varying the sequence in which multiple exoglycosidases are administered reveals information about N-glycan structure and/or composition.

In some embodiments, sequential digestion with multiple exoglycosidases reveals information about N-glycan structure and/or composition that is different from information revealed by simultaneous digestion with the same set of exoglycosidases. In some embodiments, sequential digestion with multiple exoglycosidases reveals information about N-glycan structure and/or composition that is the same information revealed by simultaneous digestion with the same set of exoglycosidases.

In some embodiments, once an exoglycosidase treatment has been carried out to completion, the structure and/or identity of cleaved glycans is analyzed. In some embodiments, at least one sample may be removed from the glycan preparation during the course of exoglycosidase treatment (e.g., at any point in time prior to completion of the exoglycosidase treatment). In some embodiments, structures and/or identities of cleaved glycans are analyzed in at least one of the removed samples. In some embodiments, the step of analyzing comprises comparing the structure and/or function of cleaved glycans in one or more of the removed samples to structure and/or function of cleaved glycans in at least one other removed sample. In some embodiments, the step of analyzing comprises comparing the structure and/or function of cleaved glycans in one or more of the removed samples to structure and/or function of cleaved glycans in a reference sample.

Structure and composition of digested N-glycans can be analyzed by any available method (e.g., chromatographic methods, mass spectrometry, nuclear magnetic resonance, capillary electrophoresis, etc.). In some embodiments, methods described herein allow for detection of N-glycan species that are present at low levels within a population of N-glycans. For example, according to the present disclosure, methods described herein allow for detection of N-glycan species that are present at levels less than 10%, less than 5%, less than 4%, less than 3%, less than 2%, less than 1.5%, less than 1%, less than 0.75%, less than 0.5%, less than 0.25%, or less than 0.1% within a population of N-glycans.

In some embodiments, methods described herein allow for detection of particular linkages that are present at low levels within a population of N-glycans. For example, according to the present disclosure, methods described herein allow for detection of particular linkages that are present at levels less than 10%, less than 5%, less than 4%, less than 3%, less than 2%, less than 1.5%, less than 1%, less than 0.75%, less than 0.5%, less than 0.25%, less than 0.1%, less than 0.075%, less than 0.05%, less than 0.025%, or less than 0.01% within a population of N-glycans.

In some embodiments, methods described herein allow for detection of relative levels of individual N-glycan species within a population of N-glycans. For example, the area under each peak of a liquid chromatograph can be measured and expressed as a percentage of the total. Such an analysis provides a relative percent amount of each N-glycan species within a population of N-glycans.

In some embodiments, methods described herein can be used to analyze the glycosylation pattern of glycoproteins that are used as therapeutic agents (e.g., interferons, colony stimulating factors, blood-clotting factors, etc.). As will be appreciated by those of ordinary skill in the art, the glycosylation patterns of these therapeutic glycoprotein agents can potentially affect their therapeutic properties. As such, it is important to accurately characterize the glycosylation pattern of an expressed glycoprotein of interest. In certain embodiments, methods in accordance with the disclosure are useful in the accurate characterization of the glycosylation pattern of such therapeutic glycoproteins.

In certain embodiments, a therapeutic glycoprotein of interest is produced in a cell and is secreted from the cell after production. Methods in accordance with the disclosure may be used to predict the glycosylation pattern of such secreted therapeutic glycoproteins.

In some embodiments, methods in accordance with the disclosure may be used to monitor the glycosylation pattern of glycoproteins during the course of their production by cells. For example, production of a glycoprotein (e.g., commercial production) may involve steps of (1) culturing cells that produce the glycoprotein, (2) obtaining samples at regular or irregular intervals throughout the process of culturing the cells, and (3) analyzing the glycosylation pattern of produced glycoproteins in each obtained sample. In some embodiments, such methods may further comprise a step of comparing the glycosylation patterns of produced glycoproteins in each obtained sample to one another. In some embodiments, such methods may further comprise a step of comparing the glycosylation patterns of produced glycoproteins in each obtained sample to the glycosylation pattern of a reference sample.

In certain embodiments, a therapeutic glycoprotein of interest is a commercially available glycoprotein (e.g., antibodies, polypeptides, interleukins, receptor analogs, receptor antagonists, etc., and/or characteristic portions thereof which are used to treat a disease, condition, or disorder). Methods in accordance with the disclosure can be used to determine the glycosylation patterns of such commercially available glycoproteins.

BRIEF DESCRIPTION OF THE DRAWING

FIG. 2: A mixture of 2AB-labeled N-glycans was subjected to treatment with sialidase, galactosidase, hexosaminidase, and fucosidase enzymes. Samples were applied to an amide column and eluted by normal phase chromatography.

DEFINITIONS

Figure 1:
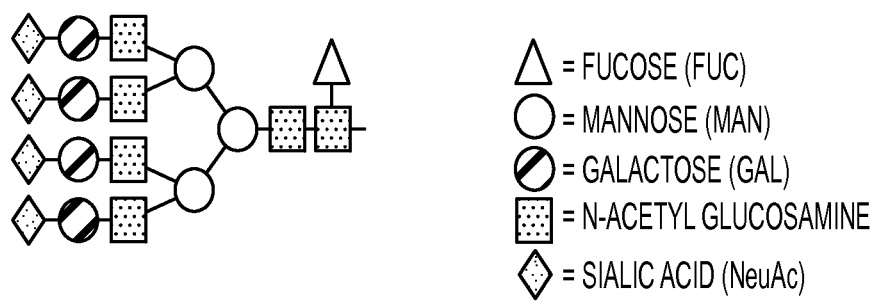
FIG. 1: Exemplary N-glycan structures.

Approximately, About, Ca.: As used herein, the terms "approximately", "about" or "ca.," as applied to one or more values of interest, refer to a value that is similar to a stated reference value. In certain embodiments, the terms "approximately", "about" or "ca.," refer to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less of the stated reference value.

Biological sample: The term "biological sample," as used herein, refers to any solid or fluid sample obtained from, excreted by or secreted by any living cell or organism, including, but not limited to, tissue culture, bioreactor sample, human or animal tissue, plants, fruits, vegetables, single-celled microorganisms (such as bacteria and yeasts) and multicellular organisms. For example, a biological sample can be a biological fluid obtained from, e.g., blood, plasma, serum, urine, bile, seminal fluid, cerebrospinal fluid, aqueous or vitreous humor, or any bodily secretion, a transudate, an exudate (e.g., fluid obtained from an abscess or any other site of infection or inflammation), or fluid obtained from a joint (e.g., a normal joint or a joint affected by disease such as a rheumatoid arthritis, osteoarthritis, gout or septic arthritis). A biological sample can also be, e.g., a sample obtained from any organ or tissue (including a biopsy or autopsy specimen), can comprise cells (whether primary cells or cultured cells), medium conditioned by any cell, tissue or organ, tissue culture.

Cell-surface glycoprotein: As used herein, the term "cell-surface glycoprotein" refers to a glycoprotein, at least a portion of which is present on the exterior surface of a cell. In some embodiments, a cell-surface glycoprotein is a protein that is positioned on the cell surface such that at least one of the glycan structures is present on the exterior surface of the cell.

Cell-surface glycan: A "cell-surface glycan" is a glycan that is present on the exterior surface of a cell. In many embodiments of the present disclosure, a cell-surface glycan is covalently linked to a polypeptide as part of a cell-surface glycoprotein. A cell-surface glycan can also be linked to a cell membrane lipid.

Glycan: As is known in the art and used herein "glycans" are sugars. Glycans can be monomers or polymers of sugar residues, but typically contain at least three sugars, and can be linear or branched. A glycan may include natural sugar residues (e.g., glucose, N-acetylglucosamine, N-acetyl neuraminic acid, galactose, mannose, fucose, hexose, arabinose, ribose, xylose, etc.) and/or modified sugars (e.g., 2'-fluororibose, 2'-deoxyribose, phosphomannose, 6'sulfo N-acetylglucosamine, etc). The term "glycan" includes homo and heteropolymers of sugar residues. The term "glycan" also encompasses a glycan component of a glycoconjugate (e.g., of a glycoprotein, glycolipid, proteoglycan, etc.). The term also encompasses free glycans, including glycans that have been cleaved or otherwise released from a glycoconjugate.

Glycan preparation: The term "glycan preparation" as used herein refers to a set of glycans obtained according to a particular production method. In some embodiments, glycan preparation refers to a set of glycans obtained from a glycoprotein preparation (see definition of glycoprotein preparation below).

Glycoconjugate: The term "glycoconjugate," as used herein, encompasses all molecules in which at least one sugar moiety is covalently linked to at least one other moiety. The term specifically encompasses all biomolecules with covalently attached sugar moieties, including for example N-linked glycoproteins, O-linked glycoproteins, glycolipids, proteoglycans, etc.

Glycoform: The term "glycoform," is used herein to refer to a particular form of a glycoconjugate. That is, when the same backbone moiety (e.g., polypeptide, lipid, etc) that is part of a glycoconjugate has the potential to be linked to different glycans or sets of glycans, then each different version of the glycoconjugate (i.e., where the backbone is linked to a particular set of glycans) is referred to as a "glycoform."

Glycolipid: The term "glycolipid" as used herein refers to a lipid that contains one or more covalently linked sugar moieties (i.e., glycans). The sugar moiety(ies) may be in the form of monosaccharides, disaccharides, oligosaccharides, and/or polysaccharides. The sugar moiety(ies) may comprise a single unbranched chain of sugar residues or may be comprised of one or more branched chains. In certain embodiments, sugar moieties may include sulfate and/or phosphate groups. In certain embodiments, glycoproteins contain O-linked sugar moieties: in certain embodiments, glycoproteins contain N-linked sugar moieties.

Glycoprotein: As used herein, the term "glycoprotein" refers to a protein that contains a peptide backbone covalently linked to one or more sugar moieties (i.e., glycans). As is understood by those skilled in the art, the peptide backbone typically comprises a linear chain of amino acid residues. In certain embodiments, the peptide backbone spans the cell membrane, such that it comprises a transmembrane portion and an extracellular portion. In certain embodiments, a peptide backbone of a glycoprotein that spans the cell membrane comprises an intracellular portion, a transmembrane portion, and an extracellular portion. In certain embodiments, methods of the present disclosure comprise cleaving a cell surface glycoprotein with a protease to liberate the extracellular portion of the glycoprotein, or a portion thereof, wherein such exposure does not substantially rupture the cell membrane. The sugar moiety(ies) may be in the form of monosaccharides, disaccharides, oligosaccharides, and/or polysaccharides. The sugar moiety(ies) may comprise a single unbranched chain of sugar residues or may comprise one or more branched chains. In certain embodiments, sugar moieties may include sulfate and/or phosphate groups. Alternatively or additionally, sugar moieties may include acetyl, glycolyl, propyl or other alkyl modifications. In certain embodiments, glycoproteins contain O-linked sugar moieties; in certain embodiments, glycoproteins contain N-linked sugar moieties. In certain embodiments, methods disclosed herein comprise a step of analyzing any or all of cell surface glycoproteins, liberated fragments (e.g., glycopeptides) of cell surface glycoproteins, cell surface glycans attached to cell surface glycoproteins, peptide backbones of cell surface glycoproteins, fragments of such glycoproteins, glycans and/or peptide backbones, and combinations thereof.

Glycosidase: The term "glycosidase" as used herein refers to an agent that cleaves a covalent bond between sequential sugars in a glycan or between the sugar and the backbone moiety (e.g., between sugar and peptide backbone of glycoprotein). In some embodiments, a glycosidase is an enzyme. In certain embodiments, a glycosidase is a protein (e.g., a protein enzyme) comprising one or more polypeptide chains. In certain embodiments, a glycosidase is a chemical cleavage agent.

Glycosylation pattern: As used herein, the term "glycosylation pattern" refers to the set of glycan structures present on a particular sample. For example, a particular glycoconjugate (e.g., glycoprotein) or set of glycoconjugates (e.g., set of glycoproteins) will have a glycosylation pattern. In some embodiments, reference is made to the glycosylation pattern of cell surface glycans. A glycosylation pattern can be characterized by, for example, the identities of glycans, amounts (absolute or relative) of individual glycans or glycans of particular types, degree of occupancy of glycosylation sites, etc., or combinations of such parameters.

Glycoprotein preparation: A "glycoprotein preparation," as that term is used herein, refers to a set of individual glycoprotein molecules, each of which comprises a polypeptide having a particular amino acid sequence (which amino acid sequence includes at least one glycosylation site) and at least one glycan covalently attached to the at least one glycosylation site. Individual molecules of a particular glycoprotein within a glycoprotein preparation typically have identical amino acid sequences but may differ in the occupancy of the at least one glycosylation sites and/or in the identity of the glycans linked to the at least one glycosylation sites. That is, a glycoprotein preparation may contain only a single glycoform of a particular glycoprotein, but more typically contains a plurality of glycoforms. Different preparations of the same glycoprotein may differ in the identity of glycoforms present (e.g., a glycoform that is present in one preparation may be absent from another) and/or in the relative amounts of different glycoforms.

N-glycan: The term "N-glycan," as used herein, refers to a polymer of sugars that has been released from a glycoconjugate but was formerly linked to the glycoconjugate via a nitrogen linkage (see definition of N-linked glycan below).

N-linked glycans: N-linked glycans are glycans that are linked to a glycoconjugate via a nitrogen linkage. A diverse assortment of N-linked glycans exists, but is typically based on the common core pentasaccharide $(Man)_3(GlcNAc)(GlcNAc)$.

O-glycan: The term "O-glycan," as used herein, refers to a polymer of sugars that has been released from a glycoconjugate but was formerly linked to the glycoconjugate via an oxygen linkage (see definition of O-linked glycan below).

O-linked glycans: O-linked glycans are glycans that are linked to a glycoconjugate via an oxygen linkage. O-linked glycans are typically attached to glycoproteins via N-acetyl-D-galactosamine (GalNAc) or via N-acetyl-D-glucosamine (GlcNAc) to the hydroxyl group of L-serine (Ser) or L-threonine (Thr). Some O-linked glycans also have modifications such as acetylation and sulfation. In some instances O-linked glycans are attached to glycoproteins via fucose or mannose to the hydroxyl group of L-serine (Ser) or L-threonine (Thr).

Phosphorylation: As used herein, the term "phosphorylation" refers to the process of covalently adding one or more phosphate groups to a molecule (e.g., to a glycan).

Protease: The term "protease" as used herein refers to an agent that cleaves a peptide bond between sequential amino acids in a polypeptide chain. In some embodiments, a protease is an enzyme (i.e., a proteolytic enzyme). In certain embodiments, a protease is a protein (e.g., a protein enzyme) comprising one or more polypeptide chains. In certain embodiments, a protease is a chemical cleavage agent.

Protein: In general, a "protein" is a polypeptide (i.e., a string of at least two amino acids linked to one another by peptide bonds). Proteins may include moieties other than amino acids (e.g., may be glycoproteins) and/or may be otherwise processed or modified. Those of ordinary skill in the art will appreciate that a "protein" can be a complete polypeptide chain as produced by a cell (with or without a signal sequence), or can be a functional portion thereof. Those of ordinary skill will further appreciate that a protein can sometimes include more than one polypeptide chain, for example linked by one or more disulfide bonds or associated by other means.

Sialic acid: The term "sialic acid," as used herein, is a generic term for the N- or O-substituted derivatives of neuraminic acid, a nine-carbon monosaccharide. The amino group of neuraminic acid typically bears either an acetyl or a glycolyl group in a sialic acid. The hydroxyl substituents present on the sialic acid may be modified by acetylation, methylation, sulfation, and phosphorylation. The predominant sialic acid is N-acetylneuraminic acid (Neu5Ac). Sialic acids impart a negative charge to glycans, because the carboxyl group tends to dissociate a proton at physiological pH. Exemplary deprotonated sialic acids are as follows:

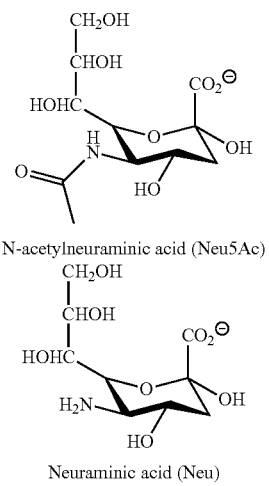

N-acetylneuraminic acid (Neu5Ac)

Neuraminic acid (Neu)

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena. To give but one particular example, when it is said that a treatment does not "substantially" rupture the cell membranes, it is meant to indicate that all or most of the cell membranes remain intact during and after the treatment, for example so that intracellular glycoproteins or glycopeptides are thus not released from the cells. In certain embodiments, the term "substantially," as applied to unruptured cell membranes, refers to condition wherein 15%, 10%, 9%, 8%, 7%, 6%, 5%, 4%, 3%, 2%, 1%, or fewer of the cells subjected to a particular treatment exhibit measurable ruptured cell membranes. In certain embodiments, the term "substantially," as applied to unruptured cell membranes, refers to condition wherein none of the cells subjected to a particular treatment exhibit measurable ruptured cell membranes.

DETAILED DESCRIPTION OF CERTAIN EMBODIMENTS

Figure 6:
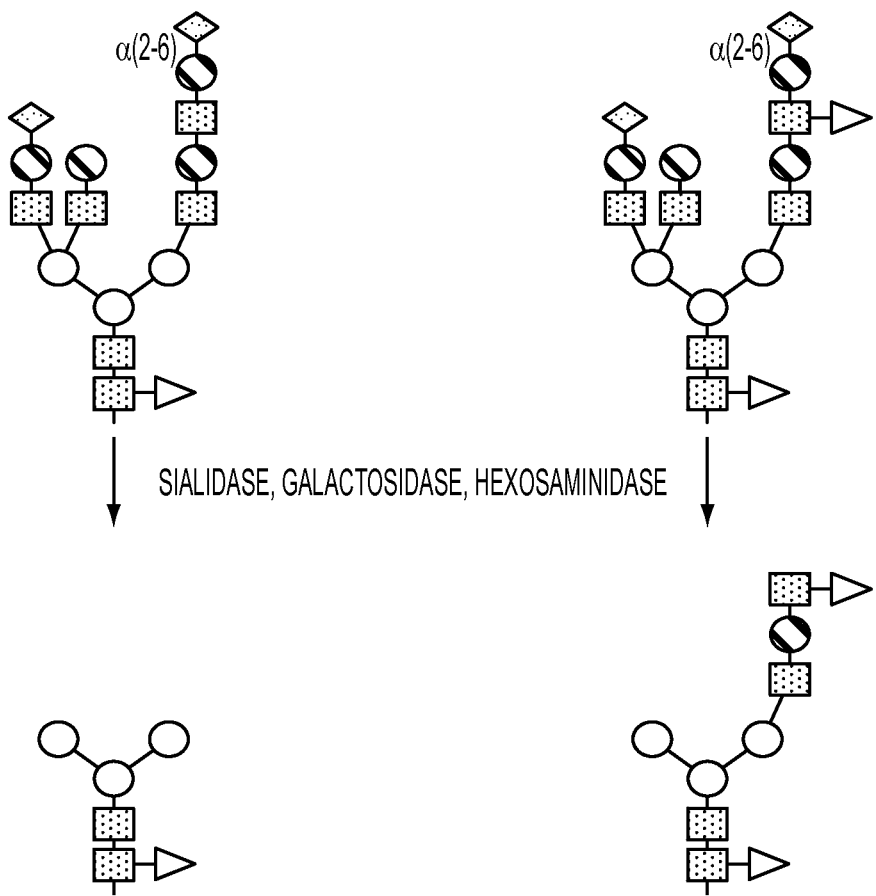
FIG. 6: Fucosylation (represented by a triangle) of glcNAc (squares) prevents hexosaminidase from being able to cleave a terminal glcNAc. Shown here are two glycan species, one with an antennary fucosylated glcNAc (right) and one without (left). After digestion with sialidase, galactosidase, and hexosaminidase, the species on the left is cleaved down to its mannose core. In contrast, the fucosylated glcNAc is unable to be cleaved away by an identical exoglycosidase treatment.

The present disclosure provides methods of analyzing the composition of N-linked glycans. According to the present disclosure, methods described herein can be used to analyze a mixture of N-glycans, and to measure the relative levels within this mixture of specific structural groups and unusual modifications (e.g., core or antennary fucose, lactosamine extensions, high mannose and hybrid glycans, sulfation, phosphorylation, etc.). For example, FIG. 6 demonstrates how antennary fucosylation prevents digestion of glcNAc by hexosaminidase. In many embodiments, the present disclosure provides methods involving steps of obtaining an N-glycan preparation; digesting N-linked glycans with exoglycosidase enzymes to specifically cleave monosaccharides from the non-reducing ends; and analyzing the cleavage products.

N-Linked Glycans

In general, a glycan refers to a carbohydrate moiety which, in some embodiments, is covalently attached to a glycoprotein. Carbohydrate moieties (e.g., oligosaccharide chains) are linked to glycoproteins in the endoplasmic reticulum and in the Golgi apparatus via either N-linkages or O-linkages. Typically, N-linked oligosaccharide chains are added to glycoproteins in the lumen of the endoplasmic reticulum (see Alberts et al., *Molecular Biology of the Cell*, 1994, incorporated herein by reference). Carbohydrate moieties are added to the amino group on the side chain of an asparagine residue contained within the target consensus sequence of Asn-X-Ser/Thr, where X may be any amino acid except proline. The initial oligosaccharide chain is usually trimmed by specific glycosidase enzymes in the endoplasmic reticulum, resulting in a short, branched core oligosaccharide composed of two N-acetylglucosamine and three mannose residues.

N-glycans can be subdivided into three distinct groups called "high mannose type," "hybrid type," and "complex type," with a common pentasaccharide core (Manp($\alpha$1,6)-(Manp($\alpha$1,3))-Manp($\beta$1,4)-GlcpNAc($\beta$1,4)-GlcpNAc($\beta$1,N)-Asn) occurring in all three groups. Modifications to the core include, for example, additional glycosylation, providing a bisecting GlcNAc, attachment of a fucosyl residue on the innermost GlcNAc, and capping with sialic acid (Neu) residues. Exemplary N-glycans are depicted in FIG. 1. As can be seen, structural variation of N-glycans mostly occurs with respect to the (up to) 4 antennae at the left hand side of the N-glycans depicted in FIG. 1. N-linked glycans are commonly found as components of peptides (i.e., a glycopeptide) and proteins (i.e., a glycoprotein).

After initial processing in the endoplasmic reticulum, glycoproteins are then transported to the Golgi where further processing may take place. Trimmed N-linked oligosaccharide chains may be modified by addition of several mannose residues, resulting in a "high-mannose oligosaccharide." Alternatively or additionally, one or more monosaccharide units of N-acetylglucosamine may be added to the core mannose subunits to form "complex oligosaccharides." Galactose may be added to N-acetylglucosamine subunits, and sialic acid subunits may be added to galactose subunits, resulting in chains that terminate with any of a sialic acid, a galactose, or an N-acetylglucosamine residue. A fucose residue may be added to an N-acetylglucosamine residue of the core oligosaccharide. Each of these additions is catalyzed by specific glycosyl transferases.

N-linked glycans are involved in a variety of cellular processes. For example, N-glycans contribute to proper protein folding in eukaryotic cells. Chaperone proteins in the endoplasmic reticulum (e.g., calnexin and calreticulin) bind to the three glucose residues present on the N-glycan core. Chaperone proteins typically aid in the folding of the protein to which the glycan is attached. Following proper folding, the three glucose residues are removed, and the glycan can move on to further processing reactions. If the protein fails to fold properly, the three glucose residues are reattached, allowing the protein to re-associate with chaperones. This cycle may repeat several times until a protein reaches it proper conformation. If a protein repeatedly fails to properly fold, it is usually excreted from the endoplasmic reticulum and degraded by cytoplasmic proteases.

Alternatively or additionally, N-glycans contribute to protein folding by steric effects. For example, cysteine residues in a peptide may be temporarily blocked from forming disulfide bonds with other cysteine residues, due to the size of a nearby glycan. Presence of an N-linked glycan, therefore, can allow a cell to control which cysteine residues will form disulfide bonds.

N-glycans can be involved in cell-cell interactions. For example, tumor cells frequently produce abnormal N-glycan structures, which can be recognized by the CD337 receptor on natural killer cells as a sign that the cell in question is cancerous.

N-glycans can be involved in targeting of degradative lysosomal enzymes to the lysosome. In particular, modification of an N-glycan with a mannose-6-phosphate residue can serve as a signal that the protein to which this glycan is attached should be targeted to the lysosome.

Thus, the present disclosure encompasses the recognition that it is important to determine the glycosylation pattern of N-glycans (e.g., N-glycans which are conjugated to glycoproteins). Methods described herein may be used to analyze the characteristics (e.g., composition and/or structure) of any N-glycan.

N-Glycan Preparations

The present disclosure provides methods of analyzing the structure and/or composition of individual glycans within a glycan preparation. A glycan preparation may be obtained by any method available in the art. In general, obtaining an N-glycan preparation comprises steps of (1) obtaining a glycoprotein preparation; and (2) obtaining an N-glycan preparation from the glycoprotein preparation. In some embodiments, obtaining an N-glycan preparation optionally comprises a step of labeling the N-glycan preparation with a detectable label.

Glycoprotein Preparations

A glycoprotein preparation may be obtained from any source including, but not limited to, therapeutic formulations (e.g., erythropoietin, insulin, human growth hormone, etc.), commercial biological products (e.g., those presented in Table 3), and biological samples. As used herein, the term "biological sample" refers to any solid or fluid sample obtained from, excreted by or secreted by any living cell or organism, including, but not limited to, tissue culture, human or animal tissue, plants, fruits, vegetables, single-celled microorganisms (such as bacteria and yeasts) and multicellular organisms. For example, a biological sample can be a biological fluid obtained from, for example, blood, plasma, serum, urine, bile, seminal fluid, cerebrospinal fluid, aqueous or vitreous humor, or any bodily secretion, a transudate, an exudate (e.g., fluid obtained from an abscess or any other site of infection or inflammation), or fluid obtained from a joint (e.g., a normal joint or a joint affected by disease such as a rheumatoid arthritis, osteoarthritis, gout or septic arthritis). A biological sample can also be, for example, a sample obtained from any organ or tissue (including a biopsy or autopsy specimen), can comprise cells (whether primary cells or cultured cells), medium conditioned by any cell, tissue or organ, tissue culture.

A glycoprotein preparation may be received by any machine, person, or entity. In some embodiments, a glycoprotein preparation may be received by a machine, which may then perform one or more tests, processes, or refinements of the glycoprotein preparation. In some embodiments, a glycoprotein preparation may be received by a person. In some embodiments, a glycoprotein preparation may be received from an outside entity. In some embodiments, a glycoprotein preparation may be received by a person or business performing characterization services for a second person or business. For example, a business may be operated in which the business receives glycoprotein preparations to be characterized from other businesses or laboratories. A glycoprotein preparation may be preprocessed in any manner. For example, a glycoprotein preparation may be preprocessed to isolate one or more glycoforms.

N-Glycan Preparation

In some embodiments, an N-glycan preparation is obtained by providing a glycoprotein population and removing N-glycans from the glycoproteins of the glycoprotein population.

In some embodiments, N-glycans are removed from glycoproteins by digestion. Generally, glycanases to be used in accordance with the present disclosure cleave between GlcNAc-Asn, GlcNAc-GlcNAc, or Man-GlcNAc residues of the core. Exemplary enzymes which can be used to remove N-glycans from glycoproteins include, but are not limited to, N-glycanase F and/or N-glycanase-A, O-glycanase and/or Endo H.

In some embodiments, N-glycans are removed from glycoproteins by chemical cleavage. To give but a few examples, hydrazine, sodium borohydride, and/or trifluoromethanesulfonic acid (TFMS) can be used to remove glycans from a glycoprotein.

Labeling N-Glycans

In some embodiments, N-glycans (e.g., N-glycans that have been removed from a glycoprotein population) can be associated with one or more detectable labels. Detectable labels are typically associated with the reducing ends of N-glycans. In some embodiments, detectable labels are fluorescent moieties. Exemplary fluorophores that can be used in accordance with the present disclosure include, but are not limited to, 2-aminobenzoic acid (2AA), 2-aminobenzamide (2AB), and/or 2-aminopurine (2AP). In general, fluorophores for use in accordance with the present disclosure are characterized by having reactivity with the reducing end of an oligosaccharide and/or monosaccharide under conditions that do not damage and/or destroy the glycan. In some embodiments, fluorescent moieties are attached to reducing ends directly. For example, direct attachment can be accomplished by direct conjugation by reductive amination. In some embodiments, fluorescent moieties are attached to reducing ends indirectly. For example, indirect attachment can be accomplished by a reactive linker arm.

In some embodiments, detectable labels comprise radioactive moieties or isotopically-labelled molecules. Exemplary radioactive moieties that can be used in accordance with the present disclosure include, but are not limited to, tritium ($^3$H), deuterium ($^2$H), and/or $^{35}$S. Typically, such moieties are directly attached to or otherwise associated with the fluorophore. To give but one example of a radioactive fluorophore, 2AP can be modified such that all hydrogens are deuterated.

Digestion of N-Linked Glycans

The present disclosure provides improved methods of determining glycosylation patterns of glycoproteins. Such methods generally involve subjecting an N-glycan population to one or more exoglycosidases and analyzing the structure and/or composition of the digestion products. In some embodiments, exoglycosidases used in accordance with the present disclosure recognize and cleave only one particular type of glycosidic linkage. In some embodiments, exoglycosidases used in accordance with the present disclosure recognize and cleave more than one particular type of glycosidic linkage.

Exoglycosidases

Exoglycosidases are enzymes which cleave terminal glycosidic bonds from the non-reducing end of glycans. They are typically highly specific to particular monosaccharide linkages and anomericity ($\alpha/\beta$). In some embodiments, neighboring branching patterns can affect exoglycosidase specificity. Exoglycosidase treatment usually results in glycans of standard antennary linkages being cleaved down to the pentasaccharide core (M3N2) containing 3 mannose and 2 glcNAc residues. However, unusually-modified species (e.g., antennary or core fucosylated species, high-mannose and hybrid glycans, lactosamine-extended glycans, sulfated glycans, phosphorylated glycans, etc.) are resistant to exoglycosidase treatment and can be chromatographically resolved and quantified relative to the M3N2 pentasaccharide.

Exemplary exoglycosidases that can be used in accordance with the present disclosure include, but are not limited to, sialidase, galactosidase, hexosaminidase, fucosidase, and mannosidase. Exoglycosidases can be obtained from any source, including commercial sources (e.g., from QA-Bio, ProZyme, Roche, Sigma, NEB, EMD, Glyko, etc.). Alternatively or additionally, exoglycosidases can be isolated and/or purified from a cellular source (e.g., bacteria, yeast, plant, etc.).

In some embodiments, exoglycosidases (e.g., sialidases, galactosidases, hexosaminidases, fucosidases, and mannosidases) can be divided into multiple categories or "subsets." In some embodiments, the different subsets display different abilities to cleave different types of linkages. Table I presents some exemplary exoglycosidases, their linkage specificities, and the organism from which each is derived. One of ordinary skill in the art will appreciate that this is an exemplary, not a comprehensive, list of exoglycosidases, and that any exoglycosidase having any linkage specificity may be used in accordance with the present disclosure.

TABLE 1

| Exoglycosidases | | | |
|---|---|---|---|
| Enzyme class | EC #* | Activity | Organism |
| α-Sialidase | 3.2.1.18 | α-2/3,6,8 (usually not linkage-specific) | Arthrobacter ureafaciens<br>Vibrio cholerae<br>Clostridium perfringens |
| | | α-2,3 (NeuAc from oligosaccharides) | Salmonella typhimurium<br>Streptococcus pneumonia |
| | | α-2/3,6 (NeuAc from complex) | Clostridium perfringens |

TABLE 1-continued

| Exoglycosidases | | | |
|---|---|---|---|
| Enzyme class | EC #* | Activity | Organism |
| β-Galactosidase | 3.2.1.23 | β-1/3,4,6 Gal linkages | Bovine testis |
| | | | Xanthamonas species |
| | | | Streptococcus species |
| | | | E. coli |
| | | β-1/4,6 Gal linkages | Jack bean |
| | | β-1,4 Gal linkage | Streptococcus pneumonia |
| | | β-1,3-Gal linkage | E. coli |
| | | | Xanthomonas species |
| | | β1/3,6-Gal linkages | Xanthomonas species |
| | | | E. coli |
| β-Hexosaminidase | 3.2.1.52 | β-1/2,3,4,6 hexosamines | Streptococcus plicatus |
| | 3.2.1.30 | | Streptococcus pneumonia |
| | | | Bacteroides |
| | | | Jack bean |
| α-Fucosidase | 3.2.1.51 | α-1-3,4-Fuc (usually de- | Xanthomonas |
| | 3.2.1.111 | glycosylate Lewis structure) | Almond meal |
| | | α-1/2,3,4,6-Fuc (usually has broad specificity) | Bovine kidney |
| | | | C. meningosepticum |
| | | α-1,6-Fuc | E. coli |
| | | α-1,2-Fuc | Xanthomonas |
| α-Mannosidase | 3.2.1.24 | α-1/2,3,6-Man | Jack bean |
| | | α-1/2,3-Man | Xanthomonas manihotis |
| | | α-1,6-Man (typically a core mannosidase) | Xanthomonas species |
| | | α-1,2-Man | Aspergillus saitoi |
| β-Mannosidase | 3.2.1.25 | α-1,4-Man | Helix pomatia |

*"EC #" refers to Enzyme Commission registration number

According to the present disclosure, an N-glycan population can be digested with any exoglycosidase or any set of exoglycosidases. In general, exoglycosidase reactions take place under conditions that are compatible with enzyme activity. For example, pH, temperature, reaction solution components and concentration (e.g., salt, detergent, etc.), and length of reaction time can be optimized in order to achieve a desired level of exoglycosidase activity.

In general, exoglycosidase reactions take place under neutral or acidic conditions. In some embodiments, exoglycosidase reactions take place under conditions that are substantially neutral. In some embodiments, neutral conditions refer to a pH ranging between approximately 6 and approximately 8. In some embodiments, neutral conditions refer to a pH of approximately 7. In some embodiments, neutral conditions refer to a pH of approximately 6.5. In some embodiments, neutral conditions refer to a pH of approximately 7.5. In some embodiments, neutral conditions refer to a pH of approximately 6. In some embodiments, neutral conditions refer to a pH of approximately 8.

In some embodiments, exoglycosidase reactions take place under conditions that are acidic. In some embodiments, acidic conditions refer to a pH of less than approximately 7. In some embodiments, acidic conditions refer to a pH ranging between approximately 1 and approximately 7. In some embodiments, acidic conditions refer to a pH ranging between approximately 2 and approximately 7. In some embodiments, acidic conditions refer to a pH ranging between approximately 3 and approximately 7. In some embodiments, acidic conditions refer to a pH ranging between approximately 4 and approximately 7. In some embodiments, acidic conditions refer to a pH ranging between approximately 5 and approximately 7. In some embodiments, acidic conditions refer to a pH ranging between approximately 6 and approximately 7.

In some embodiments, acidic conditions refer to a pH ranging between approximately 2 and approximately 6. In some embodiments, acidic conditions refer to a pH ranging between approximately 3 and approximately 6. In some embodiments, acidic conditions refer to a pH ranging between approximately 4 and approximately 6. In some embodiments, acidic conditions refer to a pH ranging between approximately 5 and approximately 6.

In some embodiments, acidic conditions refer to a pH ranging between approximately 1 and approximately 2. In some embodiments, acidic conditions refer to a pH ranging between approximately 2 and approximately 3. In some embodiments, acidic conditions refer to a pH ranging between approximately 4 and approximately 5.

In some embodiments, acidic conditions refer to a pH of approximately 6.5. In some embodiments, acidic conditions refer to a pH of approximately 6. In some embodiments, acidic conditions refer to a pH of approximately 5.5. In some embodiments, acidic conditions refer to a pH of approximately 5. In some embodiments, acidic conditions refer to a pH of approximately 4.5. In some embodiments, acidic conditions refer to a pH of approximately 4. In some embodiments, acidic conditions refer to a pH of approximately 3.5. In some embodiments, acidic conditions refer to a pH of approximately 3. In some embodiments, acidic conditions refer to a pH of approximately 2.5. In some embodiments, acidic conditions refer to a pH of approximately 2. In some embodiments, acidic conditions refer to a pH of approximately 1.5. In some embodiments, acidic conditions refer to a pH of approximately 1. In some embodiments, acidic conditions refer to a pH of approximately 0.5.

In certain embodiments, exoglycosidase reactions take place at pH ranging from approximately 5 to approximately 6. In certain embodiments, exoglycosidase reactions take place at pH of approximately 5.5. In certain embodiments, exoglycosidase reactions take place at pH ranging from approximately 6 to approximately 8.

In general, exoglycosidase reactions take place at temperatures ranging between approximately 20° C. to approximately 45° C., e.g., from approximately 30° C. to approximately 40° C. In some embodiments, exoglycosidase reactions take place at temperatures ranging between approximately 25° C. to approximately 40° C. In some embodiments, exoglycosidase reactions take place at approximately 20° C., approximately 25° C., approximately 30° C., approximately 35° C., approximately 36° C., approximately 37° C., approximately 38° C., approximately 39° C., approximately 40° C., approximately 42° C., or approximately 45° C. In certain embodiments, exoglycosidase reactions take place at temperatures ranging between approximately 35° C. to approximately 40° C. In certain embodiments, exoglycosidase reactions take place at temperatures ranging between approximately 36° C. and approximately 38° C. In certain embodiments, exoglycosidase reactions take place at temperatures of approximately 37° C.

In general, exoglycosidase reactions are performed for lengths of time ranging between approximately 10 minutes to approximately 20 hours. In some embodiments, exoglycosidase reactions are performed for approximately 10 minutes, approximately 30 minutes, approximately 1 hour, approximately 2 hours, approximately 5 hours, approximately 10 hours, approximately 12 hours, approximately 15 hours, approximately 18 hours, approximately hours, approximately 24 hours, approximately 36 hours, or approximately 48 hours. In some embodiments, exoglycosidase reactions are performed overnight.

In some embodiments, exoglycosidase reactions are performed in the presence of detergent, e.g., up to 25% detergent. Exemplary detergents that can be utilized in exoglycosidase reactions in accordance with the disclosure include sodium dodecyl sulfate (SDS), sodium lauryl sulfate (SLS), sorbitan fatty acid esters (e.g., Tween, Span, Myrj, etc.), polyethylene glycol fatty acid esters (e.g., cremophor), Brij, Triton, nonyl phenoxylpolyethoxylethanol (NP-40). In some embodiments, exoglycosidase reactions are performed in the presence of approximately 0.1%, approximately 0.5%, approximately 1%, approximately 5%, approximately 10%, approximately 15%, approximately 20%, approximately 25%, or more than 25% detergent. In some embodiments, exoglycosidase reactions are performed in the absence of any detergent.

In some embodiments, exoglycosidase reactions are performed in the presence of salt. Exemplary detergents that can be utilized in exoglycosidase reactions in accordance with the disclosure include, but are not limited to, sodium chloride, calcium chloride, sodium phosphate, sodium acetate, sodium bicarbonate, magnesium chloride, manganese chloride, and/or combinations thereof. In some embodiments, exoglycosidase reactions are performed in the presence of approximately 1 mM to approximately 500 mM salt. For example, in some embodiments, exoglycosidase reactions are performed in the presence of approximately 1 mM, approximately 2 mM, approximately 5 mM, approximately 10 mM, approximately 25 mM, approximately 50 mM, approximately 100 mM, approximately 150 mM, approximately 200 mM, approximately 250 mM, approximately 300 mM, approximately 400 mM, approximately or mM, approximately 500 mM salt. In some embodiments, exoglycosidase reactions are performed in the presence of approximately 100 mM salt. In some embodiments, exoglycosidase reactions are performed in the absence of any salt.

In certain embodiments, N-glycans are digested by subjecting a population of N-glycans to a plurality of exoglycosidases. For example, a population of N-glycans may be subjected to 2, 3, 4, 5, 6, 7, 8, 9, 10, 15, or more exoglycosidases. In some embodiments, a population of N-glycans is digested with two or more exoglycosidases that are all present in substantially equal amounts. In some embodiments, a population of N-glycans is digested with two or more exoglycosidases that are not all present in substantially equal amounts. To give but one example, a population of N-glycans may be digested with exoglycosidases A, B, and C at a ratio of 1:2:1. In some embodiments, multiple exoglycosidases are administered simultaneously. In some embodiments, multiple exoglycosidases are administered sequentially.

Simultaneous Digestion with Multiple Exoglycosidases

In some embodiments, simultaneous digestion with multiple exoglycosidases can be used to analyze glycan structure and/or function. In some cases, simultaneous digestion can be performed in order to determine the presence of particular types of linkages and/or glycan modifications. To give but one example, for the hypothetical glycan structure shown below:

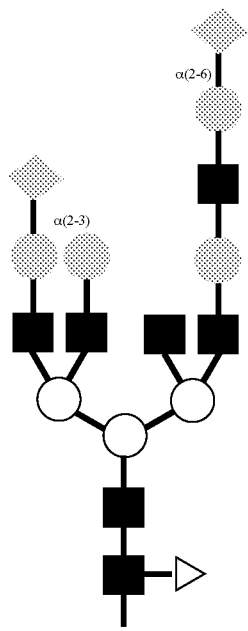

Simultaneous treatment with galactosidase and hexosaminidase is predicted to leave only the antennae which initially contained terminal sialic acid residues. These sialic acid residues may then optionally be removed, and the resulting glycan mixture analyzed by HPLC, to reveal the profile of mono-, di-, tri-, and tetra-sialyated antennary species that were present in the original mixture. Examples of simultaneous digestion approaches and analyses of such approaches are described in Example 2.

Sequential Digestion with Multiple Exoglycosidases

As another non-limiting example, N-glycans may be digested by subjecting a population of N-glycans to a first exoglycosidase for a first period of time, after which the population of N-glycans is subjected to a second exoglycosidase for a second period of time. Prior to treatment with the second exoglycosidase, the first exoglycosidase may optionally be removed and/or inactivated. By way of example, the first exoglycosidase may be inactivated incubating the exoglycosidase at a temperature for a time sufficient to inactivate it. Additionally or alternatively, the first exoglycosidase may be inactivated by incubating it with an inhibitor that is specific to the exoglycosidase (e.g., an antibody or other molecule that specifically binds the first exoglycosidase and inhibits its catalytic activity). Other methods of inactivating the first exoglycosidase will be known to those of ordinary skill in the art. In the case where the first exoglycosidase is inactivated by incubating it with a specific inhibitor, it will be appreciated that the presence of the inhibitor should not substantially inhibit the activity of the second exoglycosidase. In some embodiments, methods for inactivating or removing a first exoglycosidase before addition of a second exoglycosidase include heating the reaction mixture, cooling the reaction mixture, adding organic solvents, adding proteases, and/or combinations thereof. In some embodiments, the first exoglycosidase is removed from the reaction before addition of a second exoglycosidase, e.g., by chromatography, solid phase extraction cartridges, molecular weight filters, centrifugation, precipitation, and/or combinations thereof. One of ordinary skill in the art will recognize that these same principles apply for third, fourth, fifth, sixth, etc. exoglycosidases.

In some embodiments, sequential digestion with multiple exoglycosidases reveals information about N-glycan structure and/or composition that is different from information revealed by simultaneous digestion with the same set of exoglycosidases.

In some embodiments, sequential digestion with multiple exoglycosidases reveals information about N-glycan structure and/or composition that is the same information revealed by simultaneous digestion with the same set of exoglycosidases.

In some embodiments, varying the sequence in which multiple exoglycosidases are administered reveals information about N-glycan structure and/or composition. To give but one example, subjecting a particular N-glycan to (1) a sialidase, (2) a galactosidase, (3) a hexosaminidase, (4) a fucosidase, and (5) a mannosidase, in that particular order, might yield a set of digestion products that is different from the digestion products obtained by subjecting the same N-glycan to (1) a hexosaminidase, (2) mannosidase, (3) sialidase, (4) fucosidase, and (5) a sialidase, in that order. Performing both series of sequential digests, analyzing the different sets of digestion products obtained by both sequential digests, and comparing the different sets of digestion products (e.g. relative to one another and/or relative to a reference sample) may provide information about the structure and/or composition of the N-glycan that would not have been obtained by performing only one of the series of sequential digests and analyzing the digestion products obtained from only one of the series of sequential digests. Examples of sequential digestion approaches and analyses of such approaches are described in Example 3.

In some embodiments, the individual enzymes that constitute a set of enzymes to be used in sequential and/or simultaneous digests are chosen in order to maximize the information that may be obtained by performing digests. The treatments shown in Table 2 exemplify selection of enzymatic treatments to identify specific glycan modification on sialyated glycans.

TABLE 2

Exemplary Enzymatic Treatments for Identifying Modifications on Sialyated Glycans

| Examples of glycan modification to be identified | Examples of enzymatic treatments applicable for the identification of the selected glycan modification* |
|---|---|
| Polylactosamine | Comparison between sequential and simultaneous reactions with sialidase, galactosidase, galactosidase, hexosaminidase without sialidase, and N-acetylhexosaminidase. |

TABLE 2-continued

Exemplary Enzymatic Treatments for Identifying Modifications on Sialyated Glycans

| Examples of glycan modification to be identified | Examples of enzymatic treatments applicable for the identification of the selected glycan modification* |
|---|---|
| Antennary fucosylation | Comparison between sequential and simultaneous treatments with sialidase, galactosidase, hexosaminidase, and fucosidase. Comparison between treatments (e.g., sequential and/or simultaneous) with α-1,3 fucosidase and α-1,6,3 fucosidase. Comparison between treatments (e.g., sequential and/or simultaneous) with fucosidase followed by galactosidase or galactosidase, followed by fucosidase Comparison between treatments (e.g., sequential and/or simultaneous) with and without fucosidase. |
| Hybrid glycan | Comparison between sequential and simultaneous reactions with sialidase, galactosidase and N-acetylhexosaminidase, hexosaminidase, and mannosidase. |
| Sulfated glycans | Comparison between sequential and simultaneous reactions with sialidase, galactosidase, galactosidase, hexosaminidase without sialidase, and N-acetylhexosaminidase. |
| Phosphorylated glycans | Comparison between treatments (e.g., sequential and/or simultaneous) with and without mannosidase. |
| Sialic acid linked to GlcNAc | Comparison between sequential and simultaneous reactions with sialidase, galactosidase, galactosidase, hexosaminidase without sialidase, and N-acetylhexosaminidase. |

In some embodiments, enzymatic treatments for identifying modifications on non-sialyated glycans can be performed as described in Table 2, except that sialidase is omitted from the reactions exemplified in Table 2.

Analysis of Glycan Structure

In general, methods in accordance with the disclosure comprise subjecting a glycan preparation to an exoglycosidase treatment. In some embodiments, once an exoglycosidase treatment has been carried out to completion, the structure and/or identity of cleaved glycans is analyzed. In some embodiments, a sample may be removed from the glycan preparation during the course of exoglycosidase treatment. In some embodiments, a plurality of samples, which are separated in time (e.g. at regular or irregular intervals), may be removed from the glycan preparation during the course of the exoglycosidase treatment (e.g., at any point in time prior to completion of the exoglycosidase treatment). In some embodiments, exoglycosidase treatment comprises administration of at least one exoglycosidase, and the step of removing comprises removing at least one sample during the course of administration of at least one exoglycosidase (e.g., after the exoglycosidase has been added to the glycan preparation but before the exoglycosidase has been inactivated and/or removed from the glycan preparation). In some embodiments, exoglycosidase treatment comprises sequential administration of at least first and second exoglycosidases (e.g., first, second, third, fourth, fifth, sixth, seventh, and/or more exoglycosidases), and the step of removing comprises (i) removing at least a first sample after administration of the first exoglycosidase but before administration of the second exoglycosidase; and (ii) removing at least a second sample after administration of the second exoglycosidase. In some embodiments, the structure and/or identity of cleaved glycans is analyzed in at least one of the removed samples. In some embodiments, the step of analyzing comprises comparing the structure and/or function of cleaved glycans in one or more of the removed samples to structure and/or function of cleaved glycans in at least one other removed sample. In some embodiments, the step of analyzing comprises comparing the structure and/or function of cleaved glycans in one or more of the removed samples to structure and/or function of cleaved glycans in a reference sample.

Structure and composition of N-glycans can be analyzed by any available method. In some embodiments, N-glycan structure and composition can be analyzed by chromatographic methods, mass spectrometry (MS) methods, chromatographic methods followed by MS, electrophoretic methods, electrophoretic methods followed by MS, nuclear magnetic resonance (NMR) methods, and combinations thereof.

In some embodiments, N-glycan structure and composition can be analyzed by chromatographic methods, including but not limited to, liquid chromatography (LC), high performance liquid chromatography (HPLC), ultra performance liquid chromatography (UPLC), thin layer chromatography (TLC), amide column chromatography, and combinations thereof.

In some embodiments, N-glycan structure and composition can be analyzed by mass spectrometry (MS) and related methods, including but not limited to, tandem MS, LC-MS, LC-MS/MS, matrix assisted laser desorption ionisation mass spectrometry (MALDI-MS), Fourier transform mass spectrometry (FTMS), ion mobility separation with mass spectrometry (IMS-MS), electron transfer dissociation (ETD-MS), and combinations thereof.

In some embodiments, N-glycan structure and composition can be analyzed by electrophoretic methods, including but not limited to, capillary electrophoresis (CE), CE-MS, gel electrophoresis, agarose gel electrophoresis, acrylamide gel electrophoresis, SDS-polyacrylamide gel electrophoresis (SDS-PAGE) followed by Western blotting using antibodies that recognize specific glycan structures, and combinations thereof.

In some embodiments, N-glycan structure and composition can be analyzed by nuclear magnetic resonance (NMR) and related methods, including but not limited to, one-dimensional NMR (1D-NMR), two-dimensional NMR (2D-NMR), correlation spectroscopy magnetic-angle spinning NMR (COSY-NMR), total correlated spectroscopy NMR (TOCSY-NMR), heteronuclear single-quantum coherence NMR (HSQC-NMR), heteronuclear multiple quantum coherence (HMQC-NMR), rotational nuclear overhauser effect spectroscopy NMR (ROESY-NMR), nuclear overhauser effect spectroscopy (NOESY-NMR), and combinations thereof.

In some embodiments, methods described herein allow for detection of N-glycan species that are present at low levels within a population of N-glycans. For example, the present methods allow for detection of N-glycan species that are present at levels less than 10%, less than 5%, less than 4%, less than 3%, less than 2%, less than 1.5%, less than 1%, less than 0.75%, less than 0.5%, less than 0.25%, less than 0.1%, less than 0.075%, less than 0.05%, less than 0.025%, or less than 0.01% within a population of N-glycans.

In some embodiments, methods described herein allow for detection of particular linkages that are present at low levels within a population of N-glycans. For example, the present methods allow for detection of particular linkages that are present at levels less than 10%, less than 5%, less than 4%, less than 3%, less than 2%, less than 1.5%, less than 1%, less than 0.75%, less than 0.5%, less than 0.25%, less than 0.1%, less than 0.075%, less than 0.05%, less than 0.025%, or less than 0.01% within a population of N-glycans.

In some embodiments, methods described herein allow for detection of relative levels of individual N-glycan species within a population of N-glycans. For example, the area under each peak of a liquid chromatograph can be measured and expressed as a percentage of the total. Such an analysis provides a relative percent amount of each N-glycan species within a population of N-glycans.

Applications

The present disclosure provides methods for analyzing the structure and/or composition of any glycan. To give but one example, the present disclosure provides methods for analyzing the glycosylation pattern of a glycoprotein. The present disclosure encompasses the recognition that determining the glycosylation pattern of a glycoprotein has many potential commercial, industrial, and/or therapeutic applications.

Methods in accordance with the disclosure can be applied to glycans obtained from a wide variety of sources including, but not limited to, therapeutic formulations (e.g., erythropoietin, insulin, human growth hormone, etc.), commercial biological products (e.g., those presented in Table 3), and biological samples. A biological sample may undergo one or more analysis and/or purification steps prior to or after being analyzed according to the present disclosure. To give but a few examples, in some embodiments, a biological sample is treated with one or more proteases and/or exoglycosidases (e.g., so that glycans are released); in some embodiments, glycans in a biological sample are labeled with one or more detectable markers or other agents that may facilitate analysis by, for example, mass spectrometry or NMR. Any of a variety of separation and/or isolation steps may be applied to a biological sample in accordance with the present disclosure.

Methods of the present disclosure can be utilized to analyze glycans in any of a variety of states including, for instance, free glycans, glycoconjugates (e.g., glycopeptides, glycolipids, proteoglycans, etc.), cell-associated glycans (e.g., nucleus-, cytoplasm-, cell-membrane-associated glycans, etc.); glycans associated with cellular, extracellular, intracellular, and/or subcellular components (e.g., proteins); glycans in extracellular space (e.g., cell culture medium), etc.

Methods of the present disclosure may be used in one or more stages of process development for the production of a therapeutic or other commercially relevant glycoprotein of interest. Non-limiting examples of such process development stages that can employ methods of the present disclosure include cell selection, clonal selection, media optimization, culture conditions, process conditions, and/or purification procedure. Those of ordinary skill in the art will be aware of other process development stages.

The present disclosure can also be utilized to monitor the extent and/or type of glycosylation occurring in a particular cell culture, thereby allowing adjustment or possibly termination of the culture in order, for example, to achieve a particular desired glycosylation pattern or to avoid development of a particular undesired glycosylation pattern.

The present disclosure can also be utilized to assess glycosylation characteristics of cells or cell lines that are being considered for production of a particular desired glycoprotein (for example, even before the cells or cell lines have been engineered to produce the glycoprotein, or to produce the glycoprotein at a commercially relevant level).

For example, where the target glycoprotein is a therapeutic glycoprotein, for example having undergone regulatory review in one or more countries, it will often be desirable to monitor cultures to assess the likelihood that they will generate a product with a glycosylation pattern as close to the established glycosylation pattern of the pharmaceutical product as possible, whether or not it is being produced by exactly the same route. As used herein, "close" refers to a glycosylation pattern having at least about a 75%, 80%, 85%, 90%, 95%, 98%, or 99% correlation to the established glycosylation pattern of the pharmaceutical product. In such embodiments, samples of the production culture are typically taken at multiple time points and are compared with an established standard or with a control culture in order to assess relative glycosylation.

For example, in some embodiments, methods for monitoring production of a glycoprotein may comprise steps of (i) during production of a glycoprotein, removing at least first and second glycan-containing samples from the production system; (ii) subjecting each of the first and second glycan-containing samples to an exoglycosidase procedure, to specifically cleave monosaccharides from the non-reducing ends of N-linked glycans in the glycan-containing samples; and (iii) comparing the cleavage products obtained from the first glycan-containing sample with those obtained from the second glycan-containing sample so that differences are determined and therefore progress of glycoprotein production is monitored.

In some embodiments, methods for monitoring production of a glycoprotein involve removing at least one glycan-containing sample at some point during the exoglycosidase reaction (e.g., exoglycosidase procedure). In some embodiments, methods for monitoring production of a glycoprotein involve removing at least one glycan-containing sample before the exoglycosidase reaction has gone to completion. In some embodiments, methods for monitoring production of a glycoprotein involve removing at least one glycan-containing sample once the exoglycosidase reaction has gone to completion. In some embodiments, at least one glycan-containing sample is removed when the exoglycosidase procedure is about 10%, about 20%, about 25%, about 30%, about 40%, about 50% complete, about 60%, about 70%, about 75%, about 80%, about 90%, about 95%, about 99%, almost 100%, substantially 100%, or 100% complete. In some embodiments, at least one glycan-containing sample is removed when the exoglycosidase reaction is almost 100% complete. In some embodiments, at least one glycan-containing sample is removed when the exoglycosidase reaction is 100% complete. In some embodiments, at least one glycan-containing sample is removed before the exoglycosidase reaction is 100% complete.

In some embodiments, glycan-containing samples comprise glycoconjugates (e.g., glycoproteins). In some embodiments, at least one glycan-containing sample is removed before 100% of the glycoconjugates have been cleaved. In some embodiments, at least one glycan-containing sample is removed when 100% of the glycoconjugates have been cleaved. In some embodiments, at least one glycan-containing sample is removed when the about 10%, about 20%, about 25%, about 30%, about 40%, about 50% complete, about 60%, about 70%, about 75%, about 80%, about 90%, about 95%, about 99%, almost 100%, substantially 100%, or 100% of glycoconjugates have been cleaved. In some embodiments, at least one glycan-containing sample is removed when 100% of glycoconjugates have been cleaved. In some embodiments, at least one glycan-containing sample is removed before 100% of glycoconjugates have been cleaved.

In some embodiments, glycan-containing samples are removed at regular intervals. In some embodiments, glycan-containing samples are removed at about 30 second, about 1 minute, about 2 minute, about 5 minute, about 10 minute, about 30 minute, about 1 hour, about 2 hour, about 3 hour, about 4 hour, about 5 hour, about 10 hour, about 12 hour, or about 18 hour intervals, or at even longer intervals. In some embodiments, glycan-containing samples are removed at irregular intervals. In some embodiments, glycan-containing samples are removed at 5 hour intervals.

In some embodiments of the present disclosure, a desired glycosylation pattern will be more extensive. For example, in some embodiments, a desired glycosylation pattern shows high (e.g., greater than about 60%, about 65%, about 70%, about 75%, about 80%, about 85%, about 90%, about 95%, about 98%, about 99%, or more) occupancy of glycosylation sites; in some embodiments, a desired glycosylation pattern shows, a high degree of branching (e.g., greater than about 60%, about 65%, about 70%, about 75%, about 80%, about 85%, about 90%, about 95%, about 98%, about 99% or more have tri or tetra-antennary structures).

In some embodiments of the present disclosure, a desired glycosylation pattern will be less extensive. For example, in some embodiments, a desired cell surface glycosylation pattern shows low (e.g., less than about 50%, about 45%, about 40%, about 35%, about 30%, about 25%, about 20%, about 15%, about 15%, about 5%, about 1%, or less) occupancy of glycosylation sites; and/or a low degree of branching (e.g., less than about 20%, about 15%, about 10%, about 5%, about 1% or less have tri or tetra-antennary structures).

In some embodiments, a desired glycosylation pattern will be more extensive in some aspects and less extensive in others. For example, it may be desirable to employ a cell line that tends to produce glycoproteins with long, unbranched oligosaccharide chains. Alternatively, it may be desirable employ a cell line that tends to produce glycoproteins with short, highly branched oligosaccharide chains.

In some embodiments, a desired glycosylation pattern will be enriched for a particular type of glycan structure. For example, in some embodiments, a desired glycosylation pattern will have low levels (e.g., less than about 20%, about 15%, about 10%, about 5%, about 1%, or less) of high mannose or hybrid structures, high levels (e.g., greater than about 60%, about 65%, about 70%, about 75%, about 80%, about 85%, about 90%, about 95%, about 98%, about 99%, or more) of high mannose structures, high levels (e.g., greater than about 60%, about 65%, about 70%, about 75%, about 80%, about 85%, about 90%, about 95%, about 98%, about 99%, or more; for example at least one per glycoprotein) phosphorylated high mannose, or low levels (e.g., less than about 20%, about 15%, about 10%, about 5%, about 1%, or less) of phosphorylated high mannose.

In some embodiments, a desired glycosylation pattern will include at least about one sialic acid. In some embodiments, a desired glycosylation pattern will include a high level (e.g., greater than about 60%, about 65%, about 70%, about 75%, about 80%, about 85%, about 90%, about 95%, about 98%, about 99%, or more) of termini that are sialylated. In some embodiments, a desired glycosylation pattern that includes sialyation will show at least about 85%, about 90%, about 95%, about 98%, about 99%, or more N-acetylneuraminic acid and/or less than about 20%, about 15%, about 10%, about 5%, about 1%, or less N-glycolylneuraminic acid.

In some embodiments, a desired glycosylation pattern shows specificity of branch elongation (e.g., greater than about 60%, about 65%, about 70%, about 75%, about 80%, about 85%, about 90%, about 95%, about 98%, about 99%, or more of extension is on α1,6 mannose branches; or greater than about 60%, about 65%, about 70%, about 75%, about 80%, about 85%, about 90%, about 95%, about 98%, about 99%, or more of extension is on α1,3 mannose branches).

In some embodiments, a desired glycosylation pattern will include a low level (e.g., less than about 20%, about 15%, about 10%, about 5%, about 1%, or less) or high level (e.g., greater than about 60%, about 65%, about 70%, about 75%, about 80%, about 85%, about 90%, about 95%, about 98%, about 99%, or more) of core fucosylation.

In some embodiments, a desired glycosylation pattern will include a low level (e.g., less than about 20%, about 15%, about 10%, about 5%, about 1%, or less) or high level (e.g., greater than about 60%, about 65%, about 70%, about 75%, about 80%, about 85%, about 90%, about 95%, about 98%, about 99%, or more) of a sulfated glycan In some embodiments, a desired glycosylation pattern will include a low level (e.g., less than about 20%, about 15%, about 10%, about 5%, about 1%, or less) or high level (e.g., greater than about 60%, about 65%, about 70%, about 75%, about 80%, about 85%, about 90%, about 95%, about 98%, about 99%, or more) of a phosphorylated glycan.

In some embodiments, a desired glycosylation pattern will include a low level (e.g., less than about 20%, about 15%, about 10%, about 5%, about 1%, or less) or high level (e.g., greater than about 60%, about 65%, about 70%, about 75%, about 80%, about 85%, about 90%, about 95%, about 98%, about 99%, or more) of a sialic acid linked to an N-acetylglucosamine.

In some embodiments, a desired glycosylation pattern will include a low level (e.g., less than about 20%, about 15%, about 10%, about 5%, about 1%, or less) or high level (e.g., greater than about 60%, about 65%, about 70%, about 75%, about 80%, about 85%, about 90%, about 95%, about 98%, about 99%, or more) of an acetylated glycan.

Whether or not monitoring production of a particular target protein for quality control purposes, the present disclosure may be utilized, for example, to monitor glycosylation at particular stages of development, or under particular growth conditions.

In some embodiments, methods described herein can be used to characterize and/or control or compare the quality of therapeutic products. To give but one example, the present methodologies can be used to assess glycosylation in cells producing a therapeutic protein product. Particularly given that glycosylation can often affect the activity, bioavailability, or other characteristics of a therapeutic protein product, methods for assessing cellular glycosylation during production of such a therapeutic protein product are particularly desirable. Among other things, the present disclosure can facilitate real time analysis of glycosylation in production systems for therapeutic proteins.

Representative therapeutic glycoprotein products whose production and/or quality can be monitored in accordance with the present disclosure include, for example, any of a variety of hematologic agents (including, for instance, erythropoietin, blood-clotting factors, etc.), interferons, colony stimulating factors, antibodies, enzymes, and hormones.

Representative commercially available glycoprotein products include, for example, those presented in Table 3:

TABLE 3

Exemplary Commercially Available Glycoprotein Products

| Protein Product | Reference Drug |
|---|---|
| interferon gamma-1b | Actimmune ® |
| alteplase; tissue plasminogen activator | Activase ®/Cathflo ® |
| Recombinant antihemophilic factor | Advate |
| human albumin | Albutein ® |
| laronidase | Aldurazyme ® |
| interferon alfa-N3, human leukocyte derived | Alferon N ® |
| human antihemophilic factor | Alphanate ® |
| virus-filtered human coagulation factor IX | AlphaNine ® SD |

TABLE 3-continued

Exemplary Commercially Available Glycoprotein Products

| Protein Product | Reference Drug |
|---|---|
| Alefacept; recombinant, dimeric fusion protein LFA3-Ig | Amevive ® |
| bivalirudin | Angiomax ® |
| darbepoetin alfa | Aranesp ™ |
| bevacizumab | Avastin ™ |
| interferon beta-1a; recombinant | Avonex ® |
| coagulation factor IX | BeneFix ™ |
| Interferon beta-1b | Betaseron ® |
| Tositumomab | Bexxar ® |
| antihemophilic factor | Bioclate ™ |
| human growth hormone | BioTropin ™ |
| botulinum toxin type A | Botox ® |
| alemtuzumab | Campath ® |
| acritumomab; technetium-99 labeled | CEA-Scan ® |
| alglucerase; modified form of beta-glucocerebrosidase | Ceredase ® |
| imiglucerase; recombinant form of beta-glucocerebrosidase | Cerezyme ® |
| crotalidae polyvalent immune Fab, ovine | CroFab ™ |
| digoxin immune Fab, ovine | DigiFab ™ |
| rasburicase | Elitek ® |
| etanercept | Enbrel ® |
| epoietin alfa | Epogen ® |
| cetuximab | Erbitux ™ |
| algasidase beta | Fabrazyme ® |
| urofollitropin | Fertinex ™ |
| follitropin beta | Follistim ™ |
| teriparatide | Forteo ® |
| human somatropin | GenoTropin ® |
| glucagon | GlucaGen ® |
| follitropin alfa | Gonal-F ® |
| antihemophilic factor | Helixate ® |
| Antihemophilic Factor; Factor XIII | Hemofil ® |
| insulin | Humalog ® |
| antihemophilic factor/von Willebrand factor complex-human | Humate-P ® |
| somatotropin | Humatrope ® |
| adalimumab | HUMIRA ™ |
| human insulin | Humulin ® |
| recombinant human hyaluronidase | Hylenex ™ |
| interferon alfacon-1 | Infergen ® |
| Eptifibatide | Integrilin ™ |
| alpha-interferon | Intron A ® |
| palifermin | Kepivance |
| anakinra | Kineret ™ |
| antihemophilic factor | Kogenate ®FS |
| insulin glargine | Lantus ® |
| granulocyte macrophage colony-stimulating factor | Leukine ®/Leukine ® Liquid |
| lutropin alfa, for injection | Luveris |
| OspA lipoprotein | LYMErix ™ |
| ranibizumab | Lucentis ® |
| gemtuzumab ozogamicin | Mylotarg ™ |
| galsulfase | Naglazyme ™ |
| nesiritide | Natrecor ® |
| pegfilgrastim | Neulasta ™ |
| oprelvekin | Neumega ® |
| filgrastim | Neupogen ® |
| fanolesomab | NeutroSpec ™ (formerly LeuTech ®) |
| somatropin [rDNA] | Norditropin ®/Norditropin Nordiflex ® |
| insulin; zinc suspension; | Novolin L ® |
| insulin; isophane suspension | Novolin N ® |
| insulin, regular; | Novolin R ® |
| insulin | Novolin ® |
| coagulation factor VIIa | NovoSeven ® |
| somatropin | Nutropin ® |
| immunoglobulin intravenous | Octagam ® |
| PEG-L-asparaginase | Oncaspar ® |
| abatacept, fully human soluable fusion protein | Orencia ™ |
| muromomab-CD3 | Orthoclone OKT3 ® |
| human chorionic gonadotropin | Ovidrel ® |

TABLE 3-continued

Exemplary Commercially Available Glycoprotein Products

| Protein Product | Reference Drug |
| --- | --- |
| peginterferon alfa-2a | Pegasys ® |
| pegylated version of interferon alfa-2b | PEG-Intron ™ |
| abarelix (injectable suspension); gonadotropin-releasing hormone antagonist | Plenaxis ™ |
| epoietin alfa | Procrit ® |
| aldesleukin | Proleukin, IL-2 ® |
| somatrem | Protropin ® |
| dornase alfa | Pulmozyme ® |
| Efalizumab; selective, reversible T-cell blocker | Raptiva ™ |
| combination of ribavirin and alpha interferon | Rebetron ™ |
| Interferon beta 1a | Rebif ® |
| antihemophilic factor | Recombinate ® |
| rAHF/ntihemophilic factor | ReFacto ® |
| lepirudin | Refludan ® |
| infliximab | Remicade ® |
| abciximab | ReoPro ™ |
| reteplase | Retavase ™ |
| rituximab | Rituxan ™ |
| interferon alfa-2a | Roferon-A ® |
| somatropin | Saizen ® |
| synthetic porcine secretin | SecreFlo ™ |
| basiliximab | Simulect ® |
| eculizumab | Soliris ® |
| pegvisomant | Somavert ® |
| Palivizumab; recombinantly produced, humanized mAb | Synagis ™ |
| thyrotropin alfa | Thyrogen ® |
| tenecteplase | TNKase ™ |
| natalizumab | Tysabri ® |
| human immune globulin intravenous 5% and 10% solutions | Venoglobulin-S ® |
| interferon alfa-n1, lymphoblastoid | Wellferon ® |
| drotrecogin alfa | Xigris ™ |
| Omalizumab; recombinant DNA-derived humanized monoclonal antibody targeting immunoglobulin-E | Xolair ® |
| daclizumab | Zenapax ® |
| ibritumomab tiuxetan | Zevalin ™ |
| Somatotropin | Zorbtive ™ (Serostim ®) |

In some embodiments, the disclosure provides methods in which glycans from different sources or samples are compared with one another. In some such examples, multiple samples from the same source are obtained over time, so that changes in glycosylation patterns (and particularly in cell surface glycosylation patterns) are monitored. In some embodiments, one of the samples is a historical sample or a record of a historical sample. In some embodiments, one of the samples is a reference sample.

In some embodiments, glycans from different cell culture samples prepared under conditions that differ in one or more selected parameters (e.g., cell type, culture type [e.g., continuous feed vs batch feed, etc.], culture conditions [e.g., type of media, presence or concentration of particular component of particular medium(a), osmolarity, pH, temperature, timing or degree of shift in one or more components such as osmolarity, pH, temperature, etc.], culture time, isolation steps, etc.) but are otherwise identical, are compared, so that effects of the selected parameter on N-glycosylation patterns are determined. In certain embodiments, glycans from different cell culture samples prepared under conditions that differ in a single selected parameter are compared so that effects of the single selected parameter on glycosylation patterns is determined. Among other applications, therefore, use of techniques as described herein may facilitate determination of the effects of particular parameters on glycosylation patterns in cells.

In some embodiments, glycans from different batches of a glycoprotein of interest (e.g., a therapeutic glycoprotein), whether prepared by the same method or by different methods, and whether prepared simultaneously or separately, are compared. In such embodiments, the present disclosure facilitates quality control of glycoprotein preparation. Alternatively or additionally, some such embodiments facilitate monitoring of progress of a particular culture producing a glycoprotein of interest (e.g., when samples are removed from the culture at different time points and are analyzed and compared to one another). In some examples, multiple samples from the same source are obtained over time, so that changes in glycosylation patterns are monitored. In some embodiments, glycan-containing samples are removed at about second, about 1 minute, about 2 minute, about 5 minute, about 10 minute, about 30 minute, about 1 hour, about 2 hour, about 3 hour, about 4 hour, about 5 hour, about 10 hour, about 12 hour, or about 18 hour intervals, or at even longer intervals. In some embodiments, glycan-containing samples are removed at irregular intervals. In some embodiments, glycan-containing samples are removed at 5 hour intervals.

In some embodiments, methods in accordance with the disclosure may be used to monitor the glycosylation pattern of glycoproteins during the course of their production by cells. For example, production of a glycoprotein (e.g., commercial production) may involve steps of (1) culturing cells that produce the glycoprotein, (2) obtaining samples at regular or irregular intervals during the culturing, and (3) analyzing the glycosylation pattern of produced glycoprotein(s) in obtained sample(s). In some embodiments, such methods may comprise a step of comparing the glycosylation patterns of produced glycoprotein(s) in obtained samples to one another. In some embodiments, such methods may comprise a step of comparing glycosylation patterns of produced glycoprotein(s) in obtained sample(s) to the glycosylation pattern of a reference sample.

In any of these embodiments, features of the glycan analysis can be recorded, for example in a quality control record. As indicated above, in some embodiments, a comparison is with a historical record of a prior, or standard batch and/or with a reference sample of glycoprotein.

In some embodiments, glycans from different batches of a glycoprotein of interest (e.g. a therapeutic glycoprotein), whether prepared by the same method or by different methods, and whether prepared simultaneously or separately, are compared to one another and/or to a reference sample. In some embodiments, batch-to-batch comparison may comprise steps of (i) providing a first glycan preparation from a first batch of the glycoprotein; (ii) providing a second glycan preparation from a second batch of the glycoprotein; (iii) subjecting each of the first and second glycan preparations to an exoglycosidase procedure (e.g., sequential and/or simultaneous treatment with 1, 2, 3, 4, 5, 6, 7, or more exoglycosidases), to specifically cleave monosaccharides from the non-reducing ends of N-linked glycans in the glycan preparations; and (iv) comparing the cleavage products obtained from the first glycan preparation with the cleavage products obtained from the second preparation so that consistency of the two batches is assessed. In some embodiments, glycan preparations can be provided by removing at least one N-glycan from at least one glycoprotein from a batch and, optionally, isolating removed N-glycans. In some embodiments, glycan preparations may be labeled as described herein (e.g., fluorescently and/or radioactively; e.g., prior to and/or after isolation).

In some embodiments, the present disclosure facilitates quality control of glycoprotein preparation. Features of the glycan analysis can be recorded, for example in a quality control record. As indicated above, in some embodiments, a comparison is with a historical record of a prior or standard batch of glycoprotein. In some embodiments, a comparison is with a reference glycoprotein sample.

In certain embodiments, the present disclosure may be utilized in studies to modify the glycosylation characteristics of a cell, for example to establish a cell line and/or culture conditions with one or more desirable glycosylation characteristics. Such a cell line and/or culture conditions can then be utilized, if desired, for production of a particular target glycoconjugate (e.g., glycoprotein) for which such glycosylation characteristic(s) is/are expected to be beneficial.

In certain embodiments, techniques in accordance with the disclosure are applied to glycans that are present on the surface of cells. In some such embodiments, the analyzed glycans are substantially free of non-cell-surface glycans. In some such embodiments, the analyzed glycans, when present on the cell surface, are present in the context of one or more cell surface glycoconjugates (e.g., glycoproteins or glycolipids). In certain embodiments, the glycosylation pattern of a membrane-bound or transmembrane cell-surface glycoprotein can be determined by (1) liberating the glycoprotein by treatment with one or more proteases; (2) isolating a glycan population by digesting the liberated glycoprotein with glycanase; (3) digesting the glycan population by exoglycosidase digestion according to any of the methods described herein; and (4) analyzing the digestion products using any method available to one of ordinary skill in the art.

In some particular embodiments, cell surface glycans are analyzed in order to assess glycosylation of one or more target glycoproteins of interest, particularly where such target glycoproteins are not cell surface glycoproteins. In some embodiments, one can monitor glycosylation of a target glycoprotein without isolating the glycoprotein itself. In certain embodiments, the present disclosure provides methods of using cell-surface glycans as a readout of or proxy for glycan structures on an expressed glycoprotein of interest. In certain embodiments, such methods include, but are not limited to, post process, batch, screening or "in line" measurements of product quality. Such methods can provide for an independent measure of the glycosylation pattern of a produced glycoprotein of interest using a byproduct of the production reaction (e.g., the cells) without requiring the use of destruction of any produced glycoprotein. Furthermore, methods in accordance with the disclosure can avoid the effort required for isolation of product and the potential selection of product glycoforms that may occur during isolation.

In certain embodiments, techniques in accordance with the disclosure are applied to glycans that are secreted from cells. In some such embodiments, the analyzed glycans are produced by cells in the context of a glycoconjugate (e.g., a glycoprotein or glycolipid).

According to the present disclosure, techniques described herein can be used to detect desirable or undesirable glycans, for example to detect or quantify the presence of one or more contaminants in a product, or to detect or quantify the presence of one or more active or desired species.

In various embodiments the methods can be used to detect biomarkers indicative of, e.g., a disease state, prior to the appearance of symptoms and/or progression of the disease state to an untreatable or less treatable condition, by detecting one or more specific glycans whose presence or level (whether absolute or relative) may be correlated with a particular disease state (including susceptibility to a particular disease) and/or the change in the concentration of such glycans over time.

In certain embodiments, methods described herein facilitate detection of glycans that are present at very low levels in a source (e.g., a biological sample, glycan preparation, etc.). In such embodiments, it is possible to detect and/or optionally quantify the levels of glycans that are present at levels less than about 10%, 5%, 4%, 3%, 2%, 1.5%, 1%, 0.75%, 0.5%, 0.25%, 0.1%, 0.075%, 0.05%, 0.025%, or 0.01% within a population of glycans. In some embodiments, it is possible to detect and/or optionally quantify the levels of glycans comprising between 0.1% and 5%, e.g., between 0.1% and 2%, e.g., between 0.1% and 1% of a glycan preparation. In certain embodiments, it is possible to detect and/or optionally quantify the levels of cell surface glycans at between about 0.1 fmol to about 1 mmol.

In some embodiments, methods described herein allow for detection of particular linkages that are present at low levels within a population of glycans. For example, the present methods allow for detection of particular linkages that are present at levels less than 10%, less than 5%, less than 4%, less than 3%, less than 2%, less than 1.5%, less than 1%, less than 0.75%, less than 0.5%, less than 0.25%, less than 0.1%, less than 0.075%, less than 0.05%, less than 0.025%, or less than 0.01% within a population of glycans.

In some embodiments, methods described herein allow for detection of relative levels of individual glycan species within a population of glycans. For example, the area under each peak of a liquid chromatograph can be measured and expressed as a percentage of the total. Such an analysis provides a relative percent amount of each glycan species within a population of glycans.

In some embodiments, techniques described herein may be combined with one or more other technologies for the detection, analysis, and or isolation of glycans or glycoconjugates. For example, in certain embodiments, glycans are analyzed in accordance with the present disclosure using one or more available methods (to give but a few examples, see Anumula. Anal. Biochem. 350(1):1, 2006; Klein et al., Anal. Biochem., 179:162, 1989; and/or Townsend, R. R. Carbohydrate Analysis" High Performance Liquid Chromatography and Capillary Electrophoresis., Ed. Z. El Rassi, pp 181-209, 1995, each of which is incorporated herein by reference in its entirety). For example, in some embodiments, glycans are characterized using one or more of chromatographic methods, electrophoretic methods, nuclear magnetic resonance methods, and combinations thereof. Exemplary such methods include, for example, NMR, mass spectrometry, liquid chromatography, 2-dimensional chromatography, SDS-PAGE, antibody staining, lectin staining, monosaccharide quantitation, capillary electrophoresis, fluorophore-assisted carbohydrate electrophoresis (FACE), micellar electrokinetic chromatography (MEKC), exoglycosidase or endoglycosidase treatments, and combinations thereof. Those of ordinary skill in the art will be aware of other methods that can be used to characterize glycans together with the IMAC methods described herein.

In some embodiments, glycan structure and composition can be analyzed by chromatographic methods, including but not limited to, liquid chromatography (LC), high performance liquid chromatography (HPLC), ultra performance liquid chromatography (UPLC), thin layer chromatography (TLC), amide column chromatography, and combinations thereof.

In some embodiments, glycan structure and composition can be analyzed by mass spectrometry (MS) and related methods, including but not limited to, tandem MS, LC-MS, LC-MS/MS, matrix assisted laser desorption ionisation mass spectrometry (MALDI-MS), Fourier transform mass spectrometry (FTMS), ion mobility separation with mass spectrometry (IMS-MS), electron transfer dissociation (ETD-MS), and combinations thereof.

In some embodiments, glycan structure and composition can be analyzed by electrophoretic methods, including but not limited to, capillary electrophoresis (CE), CE-MS, gel electrophoresis, agarose gel electrophoresis, acrylamide gel electrophoresis, SDS-polyacrylamide gel electrophoresis (SDS-PAGE) followed by Western blotting using antibodies that recognize specific glycan structures, and combinations thereof.

In some embodiments, glycan structure and composition can be analyzed by nuclear magnetic resonance (NMR) and related methods, including but not limited to, one-dimensional NMR (1D-NMR), two-dimensional NMR (2D-NMR), correlation spectroscopy magnetic-angle spinning NMR (COSY-NMR), total correlated spectroscopy NMR (TOCSY-NMR), heteronuclear single-quantum coherence NMR (HSQC-NMR), heteronuclear multiple quantum coherence (HMQC-NMR), rotational nuclear overhauser effect spectroscopy NMR (ROESY-NMR), nuclear overhauser effect spectroscopy (NOESY-NMR), and combinations thereof.

The present disclosure will be more specifically illustrated with reference to the following examples. However, it should be understood that the present disclosure is not limited by these examples in any manner.

EXAMPLES

Example 1

Stepwise Digestion of N-Glycans with Exoglycosidases

Materials and Methods

Sample Preparation

N-glycans were released from a purified exemplary glycoprotein by N-glycanase F, followed by a clean-up step to remove salts, detergents, proteins, and non-glycan material. Proteins were first heat denatured and then treated with an excess of N-glycanase F overnight at 37° C. in the presence of SDS. Released glycans were isolated from the salts and enzyme using a graphitized carbon column (e.g., EnviCarb). N-glycans were fluorescently labeled on the reducing end (N-glycan-2AB) and the excess label was removed by an additional clean-up step. The 2-AB label was first dissolved in 30% acetic acid in DMSO solution and sodium cyanoborohydride was added to a final concentration of 1.2 M. About 5-10 µl of this labeling solution was added to the dried glycans and heated to 65° C. for 3 hours to allow labeling to go to completion. Labeled glycans are then isolated from free label and salts by applying the sample to a Glycoclean S cartridge, washing with 96% acetonitrile, and eluting with water.

Exoglycosidase Reactions

Glycan mixtures (0.25 nmol/µl-0.5 nmol/µl) were subjected to stepwise treatment with at least two exoglycosidases (1 µl-2 µl of sequence-grade glycosidase per 20 µl-40 µl reaction volume) selected from the group consisting of sialidase, galactosidase, hexosaminidase, and fucosidase. Typically, reactions were performed at pH ~5.5. After each step of a stepwise analysis, enzyme was inactivated before the next enzyme was added.

Analysis of Digestion Products

Digestion products were resolved by liquid chromatography (LC) on an amide column which is coupled to mass spectrometry (MS). The structural identification of glycan peaks was accomplished by matrix assisted laser desorption ionisation mass spectrometry (MALDI-MS). Glycan retention times were compared with those of known standards and with those of a glucose ladder.

Results

Figure 2A:
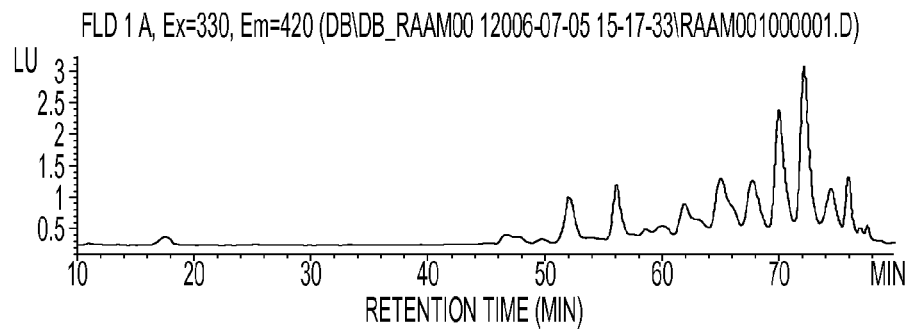
FIG. 2A N-glycan mixture separated on the amide column.
Figure 2B:
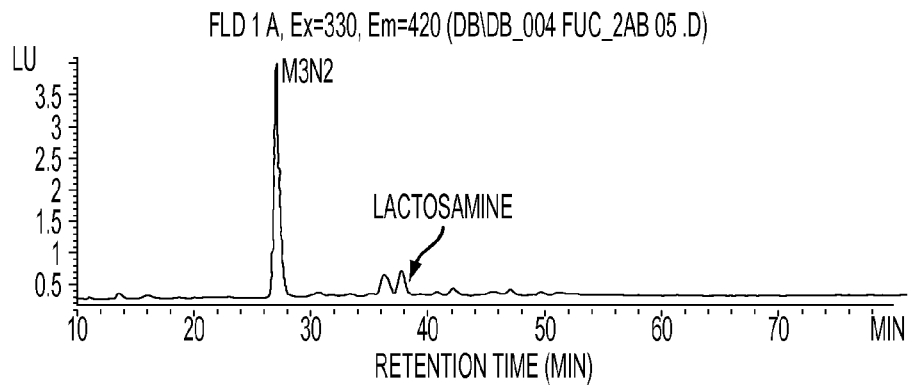
FIG. 2B N-glycans after stepwise treatment with enzymes. As shown in the chromatogram, lactosamine-extended glycans are not fully cleaved to M3N2 by this treatment. Identity of peaks was confirmed by matrix assisted laser desorption ionisation mass spectrometry (MALDI-MS).

After exhaustive stepwise treatment with exoglycosidases, the majority of N-glycans were digested to a conserved M3N2 core with some minor peaks eluting later on the chromatogram (FIG. 2B). Mass spectrometry (MS) confirmed that the minor peaks corresponded to lactosamine (FIG. 2B). FIG. 2A shows the chromatogram of the N-glycan prior to digestion.

Example 2

Simultaneous Digestion of N-Glycans with Multiple Exoglycosidases

Materials and Methods

Sample Preparation and Analysis of Digestion Products

N-glycans were prepared and digestion products were analyzed as described in Example 1.

Exoglycosidase Reactions

Glycan mixtures (0.25 nmol/µl-0.5 nmol/µl) were subjected to simultaneous treatment with at least two exoglycosidases (1µ-2 µl of sequence-grade glycosidase per 20 µl-40 µl reaction volume) selected from the group consisting of sialidase, galactosidase, hexosaminidase, and fucosidase. Typically, reactions were performed at pH ~5.5.

Results

Figure 3:
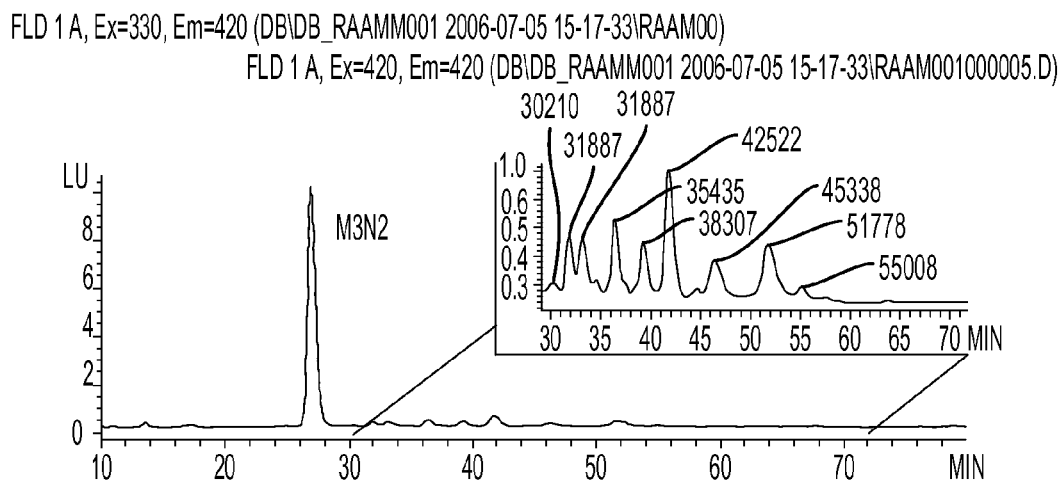
FIG. 3: Chromatogram of an N-glycan mixture following exhaustive digestion of the mixture with a simultaneous treatment with sialidase, galactosidase, hexosaminidase, and fucosidase enzymes. Samples were applied to an amide column and eluted by normal phase chromatography. Inset: close-up of the chromatogram from approximately 30 to approximately 70 minutes, scaled up to visualize lesser peaks.

When N-glycans were simultaneously treated with two or more exoglycosidases, most of the N-glycan structures collapsed to a conserved core (M3N2). Lactosamine extensions are eliminated due to the simultaneous presence of galactosidase and hexosaminidase activities. As shown in FIG. 3, there are some species with LC retention times of 30-70 minutes that were resistant to all of the exoglycosidases used. The fact that these species are refractory to conventional exoglycosidase treatment indicates that they contain unusual modifications, which can be identified by MS analysis and can be quantified by measuring the peak areas as a percentage of the total.

Example 3

Determination of the Presence of Lactosamine Groups in an N-Glycan Using Simultaneous and Sequential Exoglycosidase Digestion Sequential vs. simultaneous exoglycosidase digestion protocols can be used to obtain information about structure and/or composition of N-glycans in a glycan preparation. For example, the presence of lactosamine groups can be determined by comparing the digestion products generated by a sequential and a simultaneous digestion, as outlined in Table 4 for the hypothetical N-glycan structure:

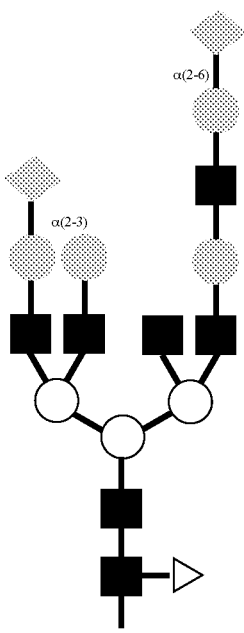

All exoglycosidases shown in Table 4 are of broad substrate specificity, that is, they will cleave off terminal sugar from a non-reducing end regardless of the type of linkage. A comparison of sequential (Q) and simultaneous (S) treatments Rx04 or Rx05 allow for the presence of polylactosamine groups in a glycan preparation to be confirmed.

identical sets of enzymes (broad specificity sialidase, galactosidase, hexosaminidase, and fucosidase). However, simultaneous (S) and sequential (Q) digests generate distinct digestion products. This example demonstrates one way in which comparing digestion products generated by simultaneous and sequential digests can provide information about glycan structure and/or composition.

Figure 7A:
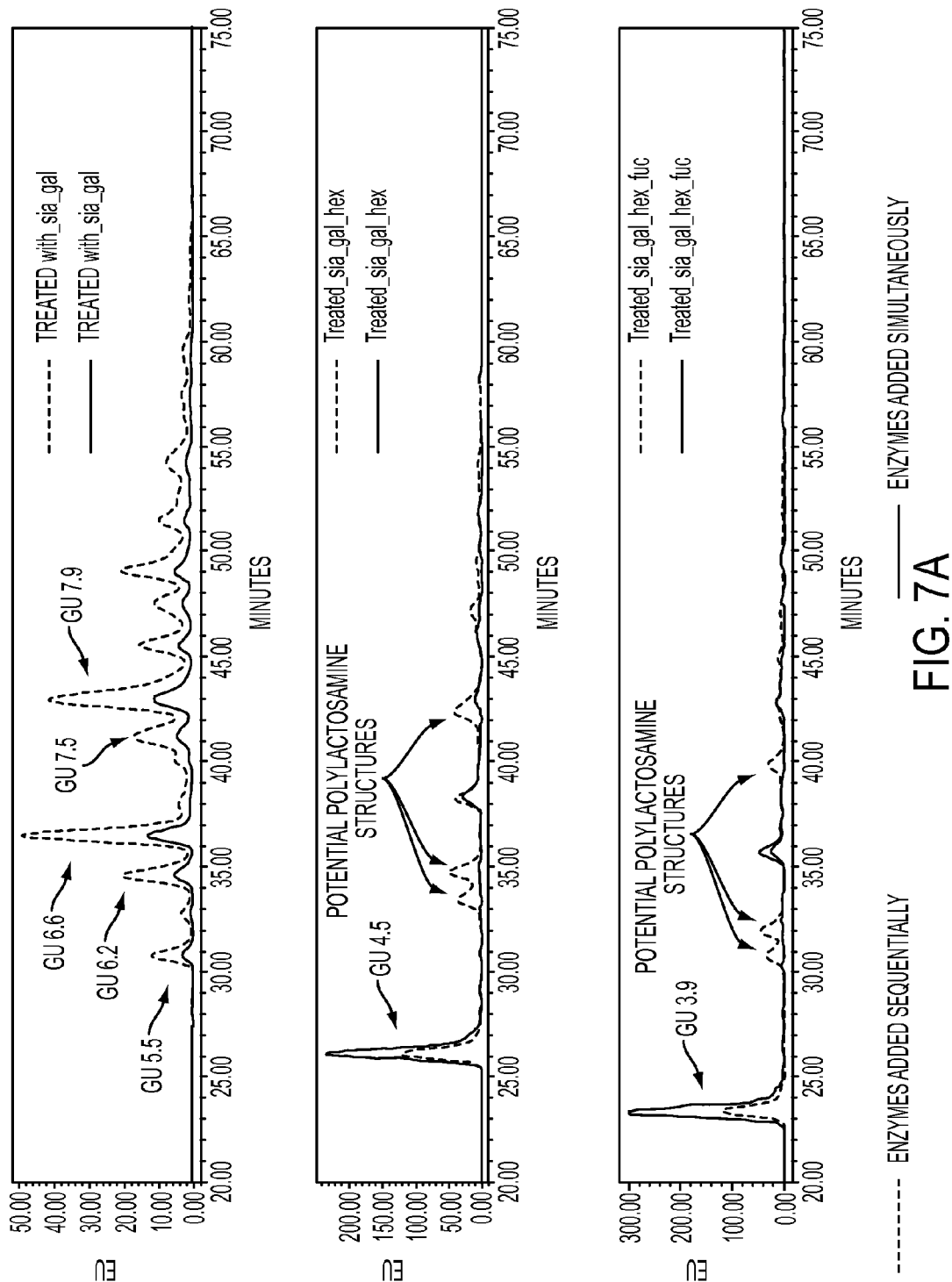
FIG. 7: Simultaneous and sequential exoglycosidase treatment to reveal hybrid and polylactosamine structures. Glycan mixtures were treated with exoglycosidases and labeled. Comparison of glycan structures that remain in the simultaneous vs. sequential cleavage is illustrated by HPLC (FIG. 7A). Glycan preparations were simultaneously or sequentially with sialidase, galactosidase (top panel), sialidase, galactosidase, and hexosaminidase (middle panel) or sialidase, galactosidase, hexosaminidase, and fucosidase (bottom panel). Comparison of glycan structures that remain in the simultaneous vs. sequential cleavage for the sialidase, galactosidase, hexosaminidase, and fucosidase reaction is illustrated by mass spectrometry (MS) (FIG. 7B). Polylactosamine structures that remain following sequential cleavage are marked in both the HPLC and the corresponding MS.
Figure 7B:
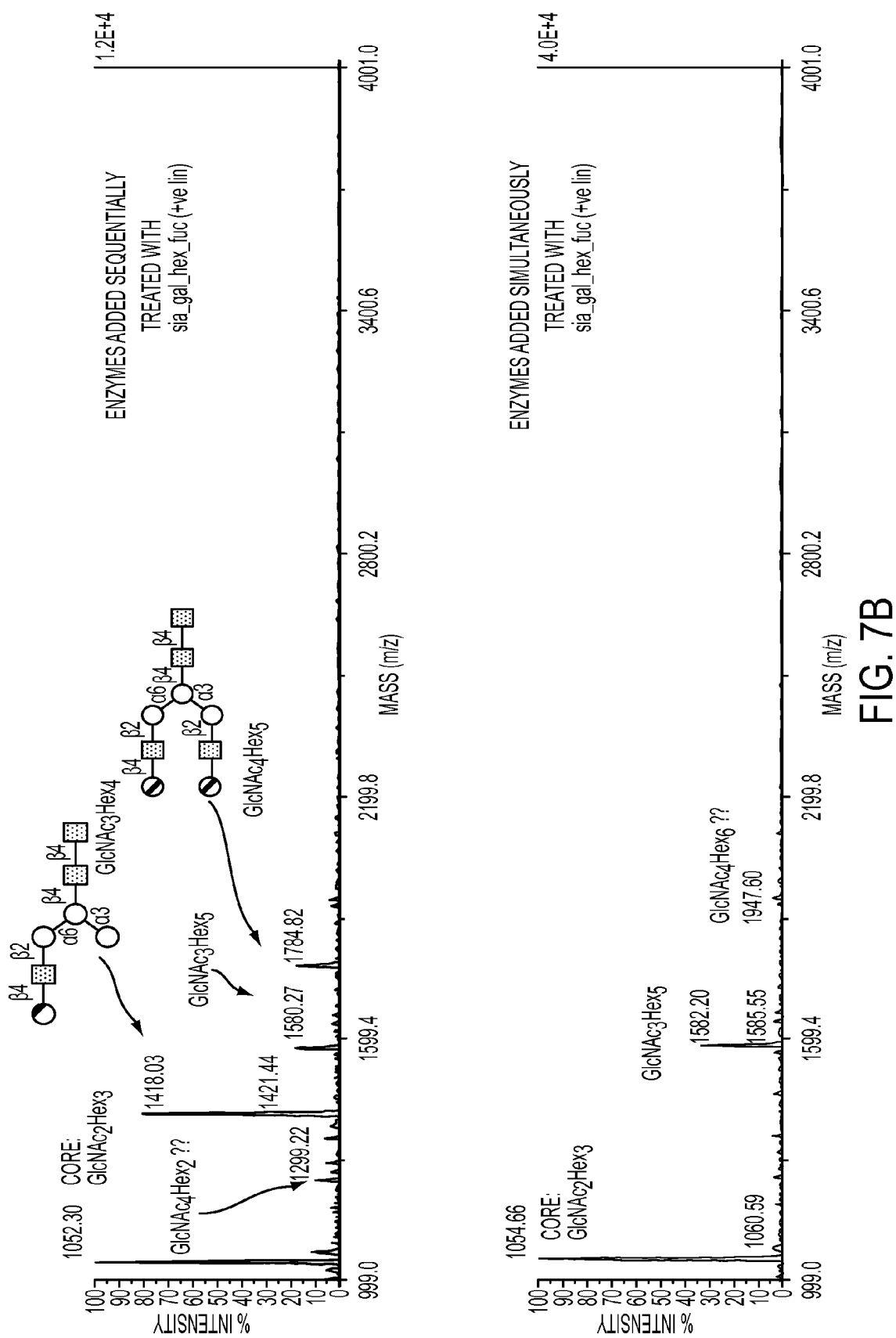

The above example is further illustrated in FIG. 7, which shows how polylactosamine structures can be elucidated by sequential vs. simultaneous digestion. In FIG. 7, the sample contains a glycan population. After simultaneous digestion of the glycan population with sialidase, galactosidase, and hexosaminidase, the majority of the glycans are cleaved down to the Man3Gn2 core structures as indicate by liquid chromatography (LC: FIG. 7A) and mass spectrometry (MS; FIG. 7B). A select few peaks with longer retention times correspond to high mannose type structures. Upon sequential digestion with sialidase, galactosidase, and hexosaminidase, however, additional peaks remain, in addition to peaks that associate with the high mannose type structures. These additional peaks correspond to glycans with a lactose attached to the Man3Gn2 core remain as indicated by the MS data. The presence of these peaks (in the sequential and not simultaneous) corresponds to polylactosamine type structures in the original sample.

Example 4

Identification of Sialic Acid Linkages in an N-Glycan Using Simultaneous and Sequential Exoglycosidase Digestion Sequential vs. simultaneous exoglycosidase digestion protocols can be used to obtain information about structure and/

TABLE 4

Sequential vs. Simultaneous Digestion with Exoglycosidases

| Enzyme | Rx01 | Rx02 S or Q | Rx03 S or Q | Rx04 S | Rx04 Q | Rx05 S | Rx05 Q |
|---|---|---|---|---|---|---|---|
| α-2/3,6,8,9-sialidase | — | X | X | X | X | X | X |
| β-1/3,4,6-galactosidase | — | — | X | X | X | X | X |
| β-2,4-hexosaminidase | — | — | — | X | X | X | X |
| α-1/3,4,6-fucosidase | — | — | — | — | — | X | X |
| Digestion Products | | | | | | | |

As shown in Table 4, Rx04 (S) and Rx04 (Q) each represent digestion of the same N-glycan with identical sets of enzymes (broad specificity sialidase, galactosidase, and hexosaminidase). However, simultaneous (S) and sequential (Q) digests generate distinct digestion products. Likewise, Rx05 (S) and Rx05 (Q) each represent digestion of the same N-glycan with or composition of N-glycans in a glycan preparation. For example, the presence and/or type of sialic acid linkages can be determined by comparing the digestion products generated by a sequential and a simultaneous digestion, as outlined in Table 5 for the hypothetical N-glycan structure:

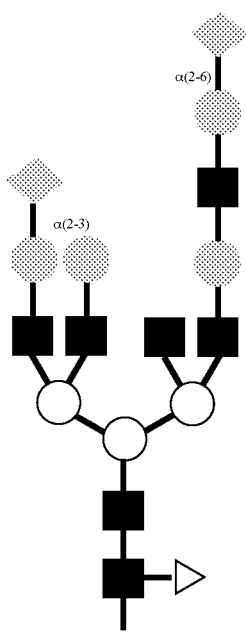

Table 5 presents a group of sialidases, each having a different substrate linkage specificity. The present example demonstrates how terminal α-2,3 sialic acid linkages can be distinguished from α-2,6-linkages.

that the 2,6-linked sialic acid is present on the polylactosamine extension, while the 2,3-linked sialic acid is on the arm with only one lactosamine. This example demonstrates one way in which comparing digestion products generated by simultaneous and sequential digests can provide information about glycan structure and/or composition.

Figure 4:
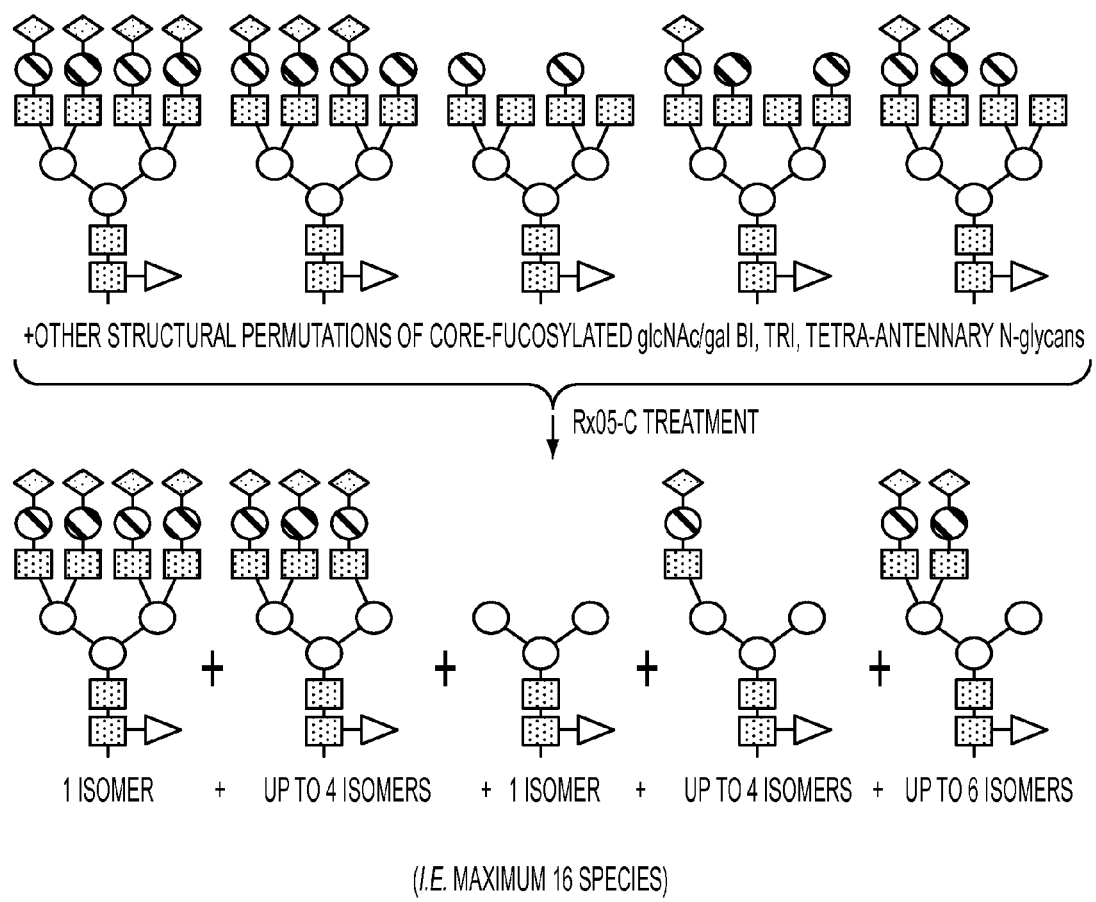
FIG. 4: Exemplary N-glycan population that is sequentially digested with broad-specificity sialidase, galactosidase, hexosaminidase, and fucosidase (Rx05-C treatment). The population of various digestion products is shown.
Figure 5:
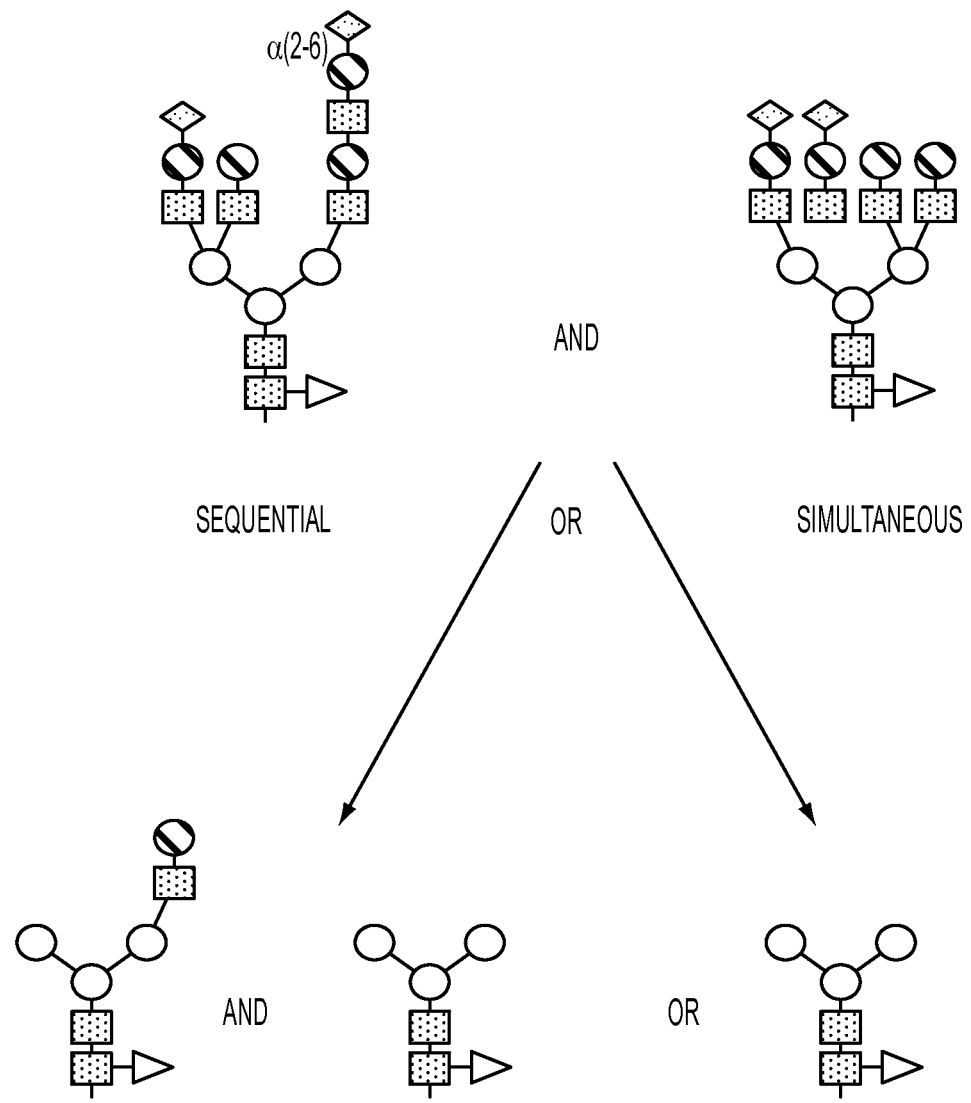
FIG. 5: Comparison of digestion products obtained after sequential (left) and simultaneous (right) digestion of a glycan population (represented by the two glycans shown at the top) with α-2/3,6,8,9-sialidase, β-1/3,4,6-galactosidase, and β-1,4-hexosaminidase. Simultaneous digestion yields the same reaction product (the mannose core) for both glycans of the glycan population. Sequential digestion yields two different digestion products. This example shows how sequential digestion can reveal information that would not be obtained from a simultaneous digestion.

In addition, as illustrated in Table 5, treatment Rx15 (Q) cleaves all non-sialyated antennae in a glycan population down to the core trimannosyl glycan. Cleavage products comprise mono-, bi-, tri- and tetra-antennary species, which can be chromatographically profiled. Such profiling provides a read-out of the antennary composition of the original glycan mixture. In particular, such profiling provides a read-out of the antennary composition of sialylated branches. With a plurality of samples, after such a glycosidase treatment has been performed, each individual glycan will have as many branches as are sialylated, and these can be separated by chromatography. This is further illustrated in FIG. 4, which represents an exemplary N-glycan population that is subjected to the digestion conditions of Rx05 (Q), as shown in Table 5. For the N-glycan population shown in FIG. 4, this example shows how sequential treatment can yield a population of digestion products. Digestion products can be analyzed, and their structures and/or compositions can be determined.

TABLE 5

Determination of Sialic Acid Linkages in N-glycans

| Enzyme | Rx11 | Rx12 S | Rx12 Q | Rx13 S | Rx13 Q | Rx14 S or Q | Rx15 S | Rx15 Q | Rx16 S or Q |
|---|---|---|---|---|---|---|---|---|---|
| α-2/3,6,8,9-sialidase | — | X | X | — | — | X | — | — | — |
| α-2/3-sialidase | — | — | — | X | X | — | — | — | X |
| β-1/3,4,6-galactosidase | — | X | X | X | X | X | X | X | X |
| β-1,4-hexosaminidase | — | X | X | X | X | — | X | X | — |
| Digestion Products | | | | | | | | | |

As shown in Table 5, Rx12 (S) and Rx12 (Q) each represent digestion of the same N-glycan with identical sets of enzymes (α-2/3,6,8,9-sialidase, β1/3,4,6-galactosidase, and β-1,4-hexosaminidase). However, simultaneous (S) and sequential (Q) digests generate distinct digestion products. As illustrated, the comparison between the sequential and the simultaneous digestion elucidates polylactosamine structures, and Example 5

Figure 8:
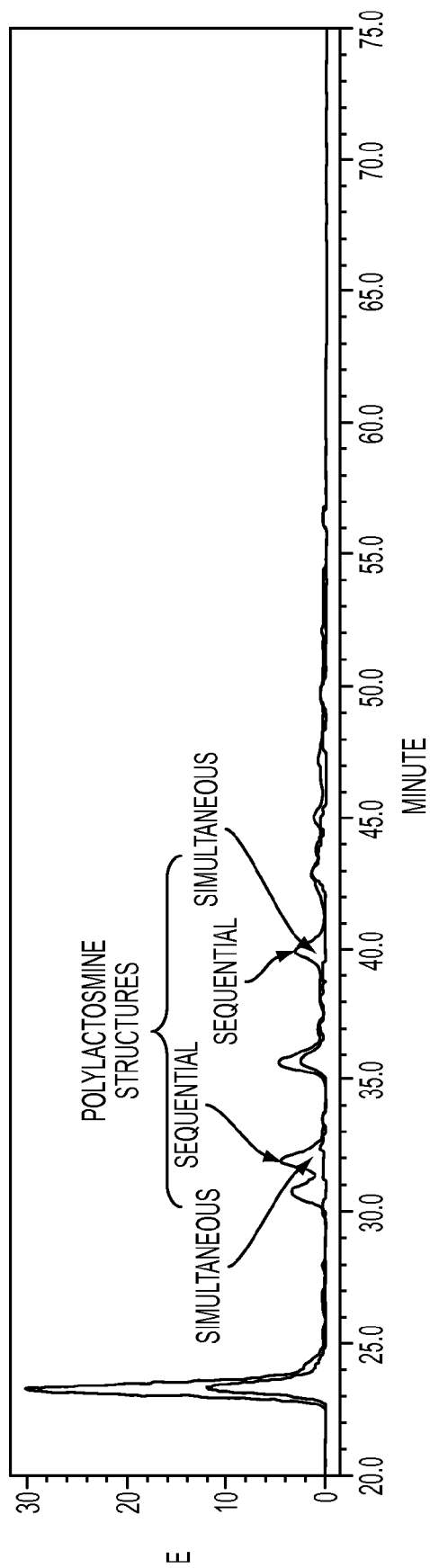
FIG. 8: Fast identification of glycans comprising polylactosamine via head-to-head comparison of chromatrograms resulting from sequential and simultaneous enzymatic treatments of the same glycan sample. Sialidase, galactosidase, hexosaminidase, and fucosidase were used for enzymatic reactions. Sequential and simultaneous treatments are indicated with arrows.
Figure 9:
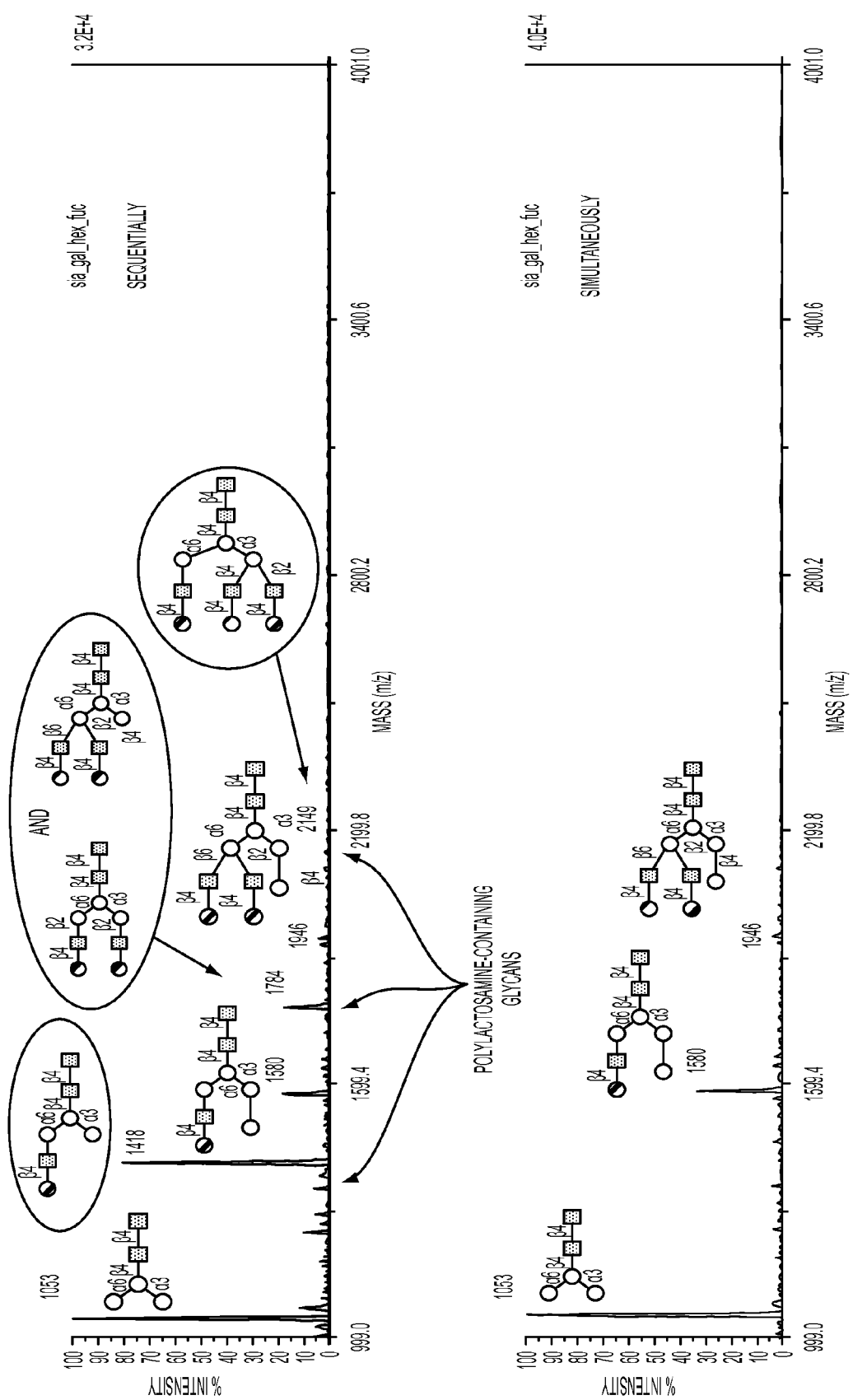
FIG. 9: Fast identification of glycans comprising polylactosamine via head-to-head comparison of MALDI-MS spectra resulting from sequential (top panel) and simultaneous (bottom panel) enzymatic treatments of the same glycan sample. Sialidase, galactosidase, hexosaminidase, and fucosidase were used for enzymatic reactions.

Identification of Fucosyl Linkages in an N-Glycan Using Simultaneous and Sequential Exoglycosidase Digestion Simultaneous exoglycosidase digestion protocols can be used to obtain information about structure and/or composition of N-glycans in a glycan preparation. For example, digestion with various combinations of exoglycosidases can be used to distinguish arm (antennary) α-1/3,4 fucosylation from core α-1,6 fucosylation of a previously-desialyated N-glycan. The effects of each treatment shown in Table 6 are illustrated in the case of the following exemplary glycan structure:

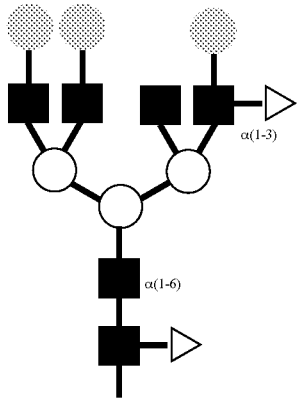

can sample. PNGase-F is an amidase that cleaves between the innermost GlcNAc and asparagine residues of high mannose, hybrid, and complex oligosaccharides from N-linked glycoproteins (Maley et al., 1989, *Anal. Biochem.,* 180:195; incorporated herein by reference). PNGase F can hydrolyze nearly all types of N-glycan chains from glycopeptides and/or glycoproteins. The resulting glycan sample was purified using activated graphitized carbon solid phase extraction cartridges. The glycan mixture was then fluorescently-labeled with 2-benzamide. The glycan sample was split into two equal parts, and each part reacted with a set of exoglycosidases (i.e., sialidase, galactosidase, and N-acetylhexosaminidase) in a simultaneous and sequential fashion, respectively. The reaction products were subsequently analyzed by normal phase fluorescent HPLC using an amide column or MALDI-MS. The results of the analysis are presented in FIG. 8 (chromatograms) and FIG. 9 (MALDI-MS).

Equivalents and Scope

Those skilled in the art will recognize, or be able to ascertain using no more than routine experimentation, many equivalents to specific embodiments in accordance with the disclosure, described herein. The scope of the present disclosure is not intended to be limited to the above Description, but rather is as set forth in the appended claims.

TABLE 6

Determination of Fucosyl Linkages

| Enzyme | Rx01 | Rx02 | Rx03 | Rx04 | Rx05 | Rx06 | Rx07 |
|---|---|---|---|---|---|---|---|
| β-1/3,4,6-galactosidase | — | X | X | — | X | X | X |
| α-1/3,4,6-fucosidase | — | X | — | — | — | X | — |
| α-1/3,4-fucosidase | — | — | X | — | — | — | X |
| β-1,4-hexosaminidase | — | X | X | X | X | — | — |
| Digestion Products | | | | | | | |

As shown in Table 6, exoglycosidase digestion with different combinations of enzymes generates various digestion products. In the example presented here, an analysis based only on mass indicates the presence of two fucose residues. However, by using the above approach, the location of the two fucose residues can be determined (i.e., one fucose is on the core and one fucose is on the branch vs. both fucose residues appearing on the branches). This example demonstrates one way in which comparing digestion products generated by simultaneous digestion can provide information about glycan structure and/or composition.

Example 6

Fast Identification of Polylactosamine-Containing Glycans

N-linked glycans were released from a model glycoprotein using Peptide: N-Glycosidase F (PNGase-F), yielding a gly- Those skilled in the art will recognize, or be able to ascertain using no more than routine experimentation, many equivalents to the specific embodiments in accordance with the disclosure described herein. The scope of the present disclosure is not intended to be limited to the above Description, but rather is as set forth in the appended claims.

In the claims articles such as "a," "an," and "the" may mean one or more than one unless indicated to the contrary or otherwise evident from the context. Thus, for example, reference to "a nanoparticle" includes a plurality of such nanoparticle, and reference to "the cell" includes reference to one or more cells known to those skilled in the art, and so forth. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process. Furthermore, it is to be understood that the disclosure encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the disclosure, or aspects in accordance with the disclosure, is/are referred to as comprising particular elements, features, etc., certain embodiments in accordance with the disclosure or aspects in accordance with the disclosure consist, or consist essentially of, such elements, features, etc. For purposes of simplicity those embodiments have not been specifically set forth in haec verba herein. It is noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments in accordance with the disclosure, to the tenth of the unit of the lower limit of the range, unless the context clearly dictates otherwise.

In addition, it is to be understood that any particular embodiment of the present disclosure that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions in accordance with the disclosure (e.g., any exoglycosidase, any glycosidic linkage, any reaction condition, any method of purification, any method of product analysis, etc.) can be excluded from any one or more claims, for any reason, whether or not related to the existence of prior art.

The publications discussed above and throughout the text are provided solely for their disclosure prior to the filing date of the present application. Nothing herein is to be construed as an admission that the inventors are not entitled to antedate such disclosure by virtue of prior disclosure.

What is claimed is:

1. A method comprising steps of:
providing a glycan preparation;
subjecting a first portion of the glycan preparation to a first exoglycosidase procedure, wherein the first exoglycosidase procedure comprises sequential treatment of the first portion with at least two exoglycosidases, wherein the first portion is exposed to each exoglycosidase one at a time;
subjecting a second portion of the glycan preparation to a second exoglycosidase procedure, wherein the second exoglycosidase procedure comprises simultaneous treatment of the second portion with the at least two exoglycosidases, wherein the second portion is exposed to each exoglycosidase at the same time;
characterizing the cleavage products of the first and second exoglycosidase procedure;
comparing the characterization of the cleavage products of the first exoglycosidase procedure to the characterization of the cleavage products of the second exoglycosidase procedure;
determining at least one glycosylation feature of the glycan preparation; and
recording the at least one determined glycosylation feature in a quality control record.

2. A method comprising steps of:
providing a glycan preparation;
subjecting a first portion of the glycan preparation to a first exoglycosidase procedure, wherein the first exoglycosidase procedure comprises sequential treatment of the first portion with at least two exoglycosidases, wherein the first portion is exposed to each exoglycosidase one at a time;
subjecting a second portion of the glycan preparation to a second exoglycosidase procedure, wherein the second exoglycosidase procedure comprises simultaneous treatment of the second portion with the at least two exoglycosidases, wherein the second portion is exposed to each exoglycosidase at the same time;
characterizing the cleavage products of the first and second exoglycosidase procedure;
comparing the characterization of the cleavage products of the first exoglycosidase procedure to the characterization of the cleavage products of the second exoglycosidase procedure;
determining at least one glycosylation feature of the glycan preparation; and
comparing the at least one determined glycosylation feature with that of a reference glycan preparation.

3. The method of claim 2, further comprising a step of comparing the at least one determined glycosylation feature with that of a historical record of the reference glycan preparation.

4. A method comprising steps of:
providing a glycan preparation from a therapeutic glycoprotein preparation;
subjecting a first portion of the glycan preparation to a first exoglycosidase procedure, wherein the first exoglycosidase procedure comprises sequential treatment of the first portion with at least two exoglycosidases, wherein the first portion is exposed to each exoglycosidase one at a time;
subjecting a second portion of the glycan preparation to a second exoglycosidase procedure, wherein the second exoglycosidase procedure comprises simultaneous treatment of the second portion with the at least two exoglycosidases, wherein the second portion is exposed to each exoglycosidase at the same time;
characterizing the cleavage products of the first and second exoglycosidase procedure;
comparing the characterization of the cleavage products of the first exoglycosidase procedure to the characterization cleavage products of the second exoglycosidase procedure; and
determining at least one glycosylation feature of the glycan preparation.

5. The method of claim 4, wherein the therapeutic glycoprotein preparation is obtained from a culture of cells producing a therapeutic glycoprotein.

6. The method of claim 5, further comprising a step of comparing the at least one determined glycosylation feature with that of a reference sample.

7. The method of claim 6, wherein the reference sample is a glycan preparation from a different batch of cells producing the therapeutic glycoprotein.

8. The method of claim 6, wherein the reference sample is a glycan preparation from the culture of cells at a different time than the therapeutic glycoprotein preparation.

9. The method of claim 6, further comprising a step of recording the result of the comparing in a quality control record for the therapeutic glycoprotein preparation.

10. The method of claim 6, wherein the at least one determined glycosylation feature is compared with a historical record of the reference sample.

11. The method of claim 4, wherein the therapeutic glycoprotein preparation is an antibody preparation.

12. The method of claim 11, wherein the antibody preparation is a preparation of alemtuzumab, etanercept, adalimumab, abatacept, infliximab, bevacizumab, rituximab, natalizumab, or cetuximab.

13. A method of characterizing a glycan preparation comprising a plurality of protein-linked N-glycans, so that one or more features of the glycan preparation is determined, the method comprising steps of:
   a) providing a glycan preparation comprising a plurality of glycoproteins, each glycoprotein comprising at least one N-glycan, which N-glycan is linked to a glycoprotein of the plurality;
      wherein the glycosylation pattern of at least one member of the plurality differs from the glycosylation pattern of at least one other member of the plurality;
   b) removing at least two N-glycans from at least one glycoprotein of the plurality;
   c) optionally, isolating removed N-glycans;
   d) subjecting the removed N-glycans to multiple separate exoglycosidase enzyme treatments, which multiple separate exoglycosidase treatments include:
      1) a sequential exoglycosidase enzyme treatment comprising sequentially exposing the preparation-glycans to each of a first and a second exoglycosidase to obtain sequential digestion results;
      2) a simultaneous exoglycosidase enzyme treatment comprising simultaneously exposing the preparation-glycans to both of the first and second exoglycosidases to obtain simultaneous digestion results;
   e) characterizing the cleavage products from each exoglycosidase treatment; and
   f) optionally, comparing the characterization of the cleavage products to a reference sample.

14. The method of claim 13, further comprising a step of recording the characterized cleavage products in a quality control record.

15. A method for comparing batches of a glycoprotein, the method comprising steps of:
   a) providing a first glycan preparation from a first batch of the glycoprotein;
   b) providing a second glycan preparation from a second batch of the glycoprotein;
   c) subjecting each of the first and second glycan preparations to multiple separate exoglycosidase enzyme treatments, which multiple separate exoglycosidase treatments include:
      1) a sequential exoglycosidase enzyme treatment comprising sequentially exposing the glycan preparation to each of a first and a second exoglycosidase to obtain sequential digestion results; and
      2) a simultaneous exoglycosidase enzyme treatment comprising simultaneously exposing the glycan preparation to both of the first and second exoglycosidases to obtain simultaneous digestion results; and
   d) comparing the sequential digestion results with the simultaneous digestion results from the first and second glycan preparations, so that differences are revealed, thereby determining the consistency of the two batches.

16. The method of claim 15, further comprising a step of recording the comparison in a quality control record.

17. A method for monitoring production of a glycoprotein, the method comprising steps of:
   a) during production of a glycoprotein, removing at least first and second glycan-containing samples from a production system;
   b) subjecting each of the first and second glycan-containing samples to multiple separate exoglycosidase enzyme treatments, which multiple separate exoglycosidase treatments include:
      (1) a sequential exoglycosidase enzyme treatment comprising sequentially exposing the glycan-containing sample to each of a first and a second exoglycosidase to obtain sequential digestion results; and
      (2) a simultaneous exoglycosidase enzyme treatment comprising simultaneously exposing the glycan-containing sample to both of the first and second exoglycosidases to obtain simultaneous digestion results; and
   c) comparing the sequential digestion results with the simultaneous digestion results from the first and second glycan-containing samples, so that differences are revealed and therefore progress of glycoprotein production is monitored.

18. The method of claim 17, further comprising a step of recording the comparison in a quality control record.

19. A method comprising steps of:
   providing a glycan preparation;
   subjecting a first portion of the glycan preparation to a first exoglycosidase procedure, wherein the first exoglycosidase procedure comprises sequential treatment of the first portion with at least two exoglycosidases, wherein the first portion is exposed to each exoglycosidase one at a time;
   subjecting a second portion of the glycan preparation to a second exoglycosidase procedure, wherein the second exoglycosidase procedure comprises simultaneous treatment of the second portion with the at least two exoglycosidases, wherein the second portion is exposed to each exoglycosidase at the same time;
   characterizing one or more cleavage products of the first and second exoglycosidase procedure;
   comparing the characterization of the one or more cleavage products of the first exoglycosidase procedure to the characterization of the one or more cleavage products of the second exoglycosidase procedure; and
   determining at least one glycosylation feature of the glycan preparation.

20. The method of claim 19, wherein the glycan preparation is from a therapeutic glycoprotein preparation.

21. The method of claim 20, wherein the therapeutic glycoprotein preparation is obtained from a culture of cells producing a therapeutic glycoprotein.

22. The method of claim 20, further comprising a step of comparing the at least one determined glycosylation feature with that of a reference sample.

23. The method of claim 20, further comprising comparing the at least one determined glycosylation feature with a historical record of a reference sample.

24. The method of claim 22, wherein the reference sample is a glycan preparation from a different batch of cells producing the therapeutic glycoprotein.

25. The method of claim 22, wherein the reference sample is a glycan preparation from the culture of cells at a different time than the therapeutic glycoprotein preparation.

26. The method of claim 22, further comprising a step of recording the result of the comparing in a quality control record for the therapeutic glycoprotein preparation.

27. The method of claim 20, wherein the therapeutic glycoprotein preparation is an antibody preparation.

28. The method of claim 27, wherein the antibody preparation is a preparation of alemtuzumab, etanercept, adalimumab, abatacept, infliximab, bevacizumab, rituximab, natalizumab, or cetuximab.

* * * * *